United States Patent
Jung et al.

(10) Patent No.: US 8,846,874 B2
(45) Date of Patent: *Sep. 30, 2014

(54) IGG FC FRAGMENT FOR A DRUG CARRIER AND METHOD FOR THE PREPARATION THEREOF

(75) Inventors: Sung Youb Jung, Suwon-si (KR); Jin Sun Kim, Gwangmyeong-si (KR); Geun Hee Yang, Suwon-si (KR); Se Chang Kwon, Gwangjin-gu (KR); Gwan Sun Lee, Songpa-gu (KR)

(73) Assignee: Hanmi Science Co., Ltd, Hwaseong-si (KR)

( * ) Notice: Subject to any disclaimer, the term of this patent is extended or adjusted under 35 U.S.C. 154(b) by 217 days.

This patent is subject to a terminal disclaimer.

(21) Appl. No.: 10/535,341

(22) PCT Filed: Nov. 13, 2004

(86) PCT No.: PCT/KR2004/002942
§ 371 (c)(1),
(2), (4) Date: Jun. 9, 2006

(87) PCT Pub. No.: WO2005/047334
PCT Pub. Date: May 26, 2005

(65) Prior Publication Data
US 2007/0041967 A1 Feb. 22, 2007

(30) Foreign Application Priority Data
Nov. 13, 2003 (KR) .................. 10-2003-0080299

(51) Int. Cl.
C07K 16/00 (2006.01)
A61K 39/40 (2006.01)
C07K 14/505 (2006.01)
A61K 47/48 (2006.01)
C07K 19/00 (2006.01)
C07K 14/56 (2006.01)
C07K 14/535 (2006.01)
C07K 14/61 (2006.01)
C07K 16/46 (2006.01)
C07K 1/00 (2006.01)

(52) U.S. Cl.
CPC ............ *C07K 16/46* (2013.01); *C07K 2319/30* (2013.01); *C07K 14/505* (2013.01); *A61K 47/48507* (2013.01); *C07K 2317/732* (2013.01); *C07K 19/00* (2013.01); *C07K 14/56* (2013.01); *C07K 14/535* (2013.01); *A61K 47/48423* (2013.01); *A61K 47/48415* (2013.01); *C07K 14/61* (2013.01); *C07K 2317/734* (2013.01)
USPC ..... 530/391.1; 530/350; 530/380; 530/391.7; 530/391.9; 424/178.1; 424/179.1; 424/180.1; 424/182.1

(58) Field of Classification Search
None
See application file for complete search history.

(56) References Cited

U.S. PATENT DOCUMENTS

| | | | |
|---|---|---|---|
| 5,045,312 A | 9/1991 | Aston et al. | 424/179.1 |
| 5,116,964 A | 5/1992 | Capon et al. | 536/23.5 |
| 5,349,053 A | 9/1994 | Landolfi | 530/351 |
| 5,585,097 A | 12/1996 | Bolt et al. | 424/133.1 |
| 5,605,690 A | 2/1997 | Jacobs et al. | 424/134.1 |
| 5,672,688 A | 9/1997 | Kobayashi et al. | 530/391.7 |
| 5,712,121 A | 1/1998 | Devos et al. | 435/69.7 |
| 5,723,125 A | 3/1998 | Chang et al. | 424/134.1 |
| 5,908,626 A | 6/1999 | Chang et al. | 424/134.1 |
| 6,030,613 A | 2/2000 | Blumberg et al. | 424/134.1 |
| 6,034,223 A * | 3/2000 | Maddon et al. | 530/391.7 |
| 6,277,375 B1 | 8/2001 | Ward | 424/133.1 |
| 6,410,008 B1 | 6/2002 | Strom et al. | 424/85.2 |
| 6,444,792 B1 | 9/2002 | Gray et al. | 530/387.3 |
| 6,451,313 B1 | 9/2002 | Maddon et al. | 424/185.1 |
| 6,660,843 B1 | 12/2003 | Feige et al. | 530/391.7 |
| 6,737,056 B1 * | 5/2004 | Presta | 424/133.1 |
| 6,756,480 B2 * | 6/2004 | Kostenuik et al. | 530/387.1 |
| 8,124,094 B2 * | 2/2012 | Kim et al. | 424/178.1 |
| 2001/0053539 A1 | 12/2001 | Lauffer et al. | 435/69.7 |
| 2002/0037558 A1 | 3/2002 | Lo et al. | 435/69.6 |
| 2002/0081664 A1 | 6/2002 | Lo et al. | 435/69.5 |
| 2003/0073164 A1 | 4/2003 | Simmons et al. | 435/69.1 |
| 2003/0082679 A1 | 5/2003 | Sun et al. | 435/69.1 |
| 2003/0082749 A1 | 5/2003 | Sun et al. | 435/70.21 |
| 2004/0044188 A1 | 3/2004 | Feige et al. | 530/388.23 |
| 2004/0053845 A1 | 3/2004 | Feige et al. | 514/12 |
| 2006/0153839 A1 * | 7/2006 | Mohamed et al. | 424/143.1 |

FOREIGN PATENT DOCUMENTS

| | | |
|---|---|---|
| EP | 0227110 | * 12/1986 |
| EP | 0 464 533 B1 | 1/1992 |
| EP | 0 580 171 A2 | 1/1994 |
| JP | 62-201582 | 9/1987 |
| JP | 2003-508023 A | 3/2003 |
| JP | 2003-521925 A | 7/2003 |
| JP | 2003-530070 A | 10/2003 |
| JP | 2003-530870 A | 10/2003 |
| JP | 2003-531632 A | 10/2003 |
| JP | 2004-537262 A | 12/2004 |

(Continued)

OTHER PUBLICATIONS

Jendeberg et al. J. Immunol. Method. 1997. 201:25-34.*

(Continued)

*Primary Examiner* — Chun Dahle
(74) *Attorney, Agent, or Firm* — Sughrue Mion, PLLC

(57) ABSTRACT

Disclosed is an IgG Fc fragment useful as a drug carrier. Also, the present invention discloses a recombinant vector expressing the IgG Fc fragment, a transformant transformed with the recombinant vector, and a method of preparing an IgG Fc fragment, comprising culturing the transformant. When conjugated to a certain drug, the IgG Fc fragment improves the in vivo duration of action of the drug and minimizes the in vivo activity reduction of the drug.

4 Claims, 11 Drawing Sheets

(56) References Cited

FOREIGN PATENT DOCUMENTS

| | | |
|---|---|---|
| JP | 2005-501052 A | 1/2005 |
| KR | 10-0249572 B1 | 12/1999 |
| KR | 10-0316347 | 11/2001 |
| KR | 2003-0009464 A1 | 1/2003 |
| OA | 02/46227 A2 | 6/2002 |
| WO | 97/24137 A1 | 7/1997 |
| WO | 99/02709 A1 | 1/1999 |
| WO | 00/23472 A2 | 4/2000 |
| WO | 00/40615 A2 | 7/2000 |
| WO | 00/69913 A1 | 11/2000 |
| WO | 01/02440 A1 | 1/2001 |
| WO | 01/03737 A1 | 1/2001 |
| WO | WO 01/03737 A1 * | 1/2001 |
| WO | 01/81415 A2 | 11/2001 |
| WO | 02/057435 A2 | 7/2002 |
| WO | 02/066514 A2 | 8/2002 |
| WO | 03/057134 A2 | 7/2003 |
| WO | 03/064992 A2 | 8/2003 |

OTHER PUBLICATIONS

Veronese et al. Drug Discovery Today: Technologies 2009 doi:10.1016/j.ddtec.2009.02.002. pp. e1-e8.*

Bentz et al., "Improved local delivery of TGF-β2 by binding to injectable fibrillar collagen via difunctional polyethylene glycol," *J. Biomed. Mat. Res.* 39(4):539-548, 1998.

van der Poll et al., "Effect of a Recombinant Dimeric Tumor Necrosis Factor Receptor on Inflammatory Responses to Intravenous Endotoxin in Normal Humans," *Blood* 89(10):3727-3734, May 15, 1997.

Matsuda et al., "Proton Nuclear Magnetic Resonance Studies of the Structure of the Fc Fragment of Human Immunoglobulin G1: Comparisons of Native and Recombinant Proteins," Molecular Immunology, 1990, vol. 27, No. 6, pp. 571-579.

Kitai et al., "Extracellular Production of Human Immunoglobulin G Fc Region (hIgG-Fc) by *Escherichia coli*," Applied Microbiology Biotechnology, 1998, vol. 28, pp. 52-56.

Japanese Office Action issued in corresponding JP Application No. 2006-539396, dated Sep. 10, 2010.

Stevenson et al., "Conjugation of Human Fcγ in Closed-Hinge or Open-Hinge Configuration to Fab'y and Analogous Ligands," The American Association of Immunologists, 1997, pp. 2242-2250.

Andrew P. Chapman, "PEGylated antibodies and antibody fragments for improved therapy: a review," Advanced Drug Delivery Reviews, 2002, vol. 54, pp. 531-545.

Japanese Patent Office, Japanese Office Action issued in corresponding JP Application No. 2011-202199, dated Jun. 25, 2013.

European Patent Office, European Search Report issued in corresponding EP Application No. 10 009 129.7, dated Oct. 14, 2010.

* cited by examiner

Protein A(stepwise pH elution)

M: Molecular size marker
Lane 1: Fc
Lane 2: Physiologically active protein
Lane 3: Physiologically active protein-PEG-Fc conjugate MW (Da)

Time (min)

Time (min)

Time (min)

IGG FC FRAGMENT FOR A DRUG CARRIER AND METHOD FOR THE PREPARATION THEREOF

TECHNICAL FIELD

The present invention relates to an IgG Fc fragment useful as a drug carrier, and more particularly, to IgG2 Fc and IgG4 Fc fragments, combinations thereof and hybrids thereof. Also, the present invention is concerned with an expression vector for expressing the IgG Fc fragment, a transformant transformed with the said expression vector and a method for preparing an immunoglobulin Fc fragment by culturing the said transformant.

BACKGROUND ART

In the past, a large number of pharmacologists and chemists made efforts to chemically alter and/or modify the in vivo activity of naturally existing, physiologically active molecules. These efforts mainly focused on increasing or prolonging certain in vivo activity, reducing toxicity, eliminating or reducing side effects, or modifying specific physiological activities of the physiologically active substances. When a physiologically active substance is chemically modified, it loses some or most of its physiological activities in many cases. However, in some cases, the modification could result in an increase or change in physiological activity. In this regard, many studies have been focused on chemical modification capable of achieving desired physiological activity, and most of such studies have involved covalently bonding a physiologically active substance (drug) to a physiologically acceptable carrier.

For example, International Pat. Publication No. WO 01/93911 employs a polymer having a plurality of acid moieties as a drug carrier. International Pat. Publication No. WO 03/00778 discloses an anionic group-containing amphiphilic block copolymers that, when used as a drug carrier for a cationic drug, improve the stability of the drug. European Pat. No. 0 681 481 describes a method of improving the properties of basic drugs by using cyclodextrin and acids as carriers. On the other hand, hydrophobic drugs have low stability in vivo mainly due to their low aqueous solubility. To improve the low aqueous solubility of hydrophobic drugs, International Pat. Publication No. WO 04/064731 employs a lipid as a carrier. However, to date, there is no report for the use of an immunoglobulin Fc fragment as a drug carrier.

Typically, since polypeptides are relatively easily denatured due to their low stability, degraded by proteolytic enzymes in the blood and easily eliminated through the kidney or liver, protein medicaments, including polypeptides as pharmaceutically effective components, need to be frequently administered to patients to maintain desired blood level concentrations and titers. However, this frequent administration of protein medicaments, especially through injection causes pain for patients. To solve these problems, many efforts have been made to improve the serum stability of protein drugs and maintain the drugs in the blood at high levels for a prolonged period of time, and thus maximize the pharmaceutical efficacy of the drugs. Pharmaceutical compositions with sustained activity, therefore, need to increase the stability of protein drugs and maintain the titers at sufficiently high levels without causing immune responses in patients.

To stabilize proteins and prevent enzymatic degradation and clearance by the kidneys, a polymer having high solubility, such as polyethylene glycol (hereinafter, referred to simply as "PEG"), was conventionally used to chemically modify the surface of a protein drug. By binding to specific or various regions of a target protein, PEG stabilizes the protein and prevents hydrolysis, without causing serious side effects (Sada et al., *J. Fermentation Bioengineering* 71: 137-139, 1991). However, despite its capability to enhance protein stability, this PEG coupling has problems such as greatly reducing the number titers of physiologically "active" proteins. Further the yield decreases with the increasing molecular weight of PEG due to the reduced reactivity with the proteins.

Recently, polymer-protein drug conjugates have been suggested. For example, as described in U.S. Pat. No. 5,738,846, a conjugate can be prepared by linking an identical protein drug to both ends of PEG to improve the activity of the protein drug. Also, as described in International Pat. Publication No. WO 92/16221, two different protein drugs can be linked to both ends of PEG to provide a conjugate having two different activities. The above methods, however, were not very successful in sustaining the activity of protein drugs.

On the other hand, Kinstler et al. reported that a fusion protein prepared by coupling granulocyte-colony stimulating factor (G-CSF) to human albumin showed improved stability (Kinstler et al., *Pharmaceutical Research* 12(12): 1883-1888, 1995). In this publication, however, since the modified drug, having a G-CSF-PEG-albumin structure, only showed an approximately four-fold increase in residence time in the body and a slight increase in serum half-life compared to the single administration of the native G-CSF, it has not been industrialized as an effective long-acting formulation for protein drugs.

An alternative method for improving the in vivo stability of physiologically active proteins is by linking a gene of physiologically active protein to a gene encoding a protein having high serum stability by genetic recombination technology and culturing the cells transfected with the recombinant gene to produce a fusion protein. For example, a fusion protein can be prepared by conjugating albumin, a protein known to be the most effective in enhancing protein stability, or its fragment to a physiologically active protein of interest by genetic recombination (International Pat. Publication Nos. WO 93/15199 and WO 93/15200, European Pat. Publication No. 413,622). A fusion protein of interferon-alpha and albumin, developed by the Human Genome Science Company and marketed under the trade name of 'Albuferon™', increased the half-life from 5 hours to 93 hours in monkeys, but it was known to be problematic because it decreased the in vivo activity to less than 5% of unmodified interferon-alpha (Osborn et al., *J. Phar. Exp. Ther.* 303(2): 540-548, 2002). There has been no report of good technology that enhance both the in vivo duration of action and the stability of protein drugs as well as maintaining the in vivo physiological activity of the drugs.

On the other hand, immunoglobulins and their fragments were employed to enhance the stability of protein drugs. For example, U.S. Pat. No. 5,045,312 discloses a method of increasing the activity of a growth hormone compared to an unmodified growth hormone by conjugating human growth hormone to serum albumin or rat immunoglobulin using a crosslinking agent. Also, other attempts were made to fuse a protein drug to an immunoglobulin Fc fragment. For example, interferon (Korean Pat. Laid-open Publication No. 2003-9464), and interleukin-4 receptor, interleukin-7 receptor or erythropoietin (EPO) receptor (Korean Pat. Registration No. 249572) were previously expressed in mammals in a form fused to an immunoglobulin Fc fragment. International Pat. Publication No. WO 01/03737 describes a fusion protein comprising a cytokine or growth factor linked to an immunoglobulin Fc fragment through peptide linkage. In addition, U.S. Pat. No. 5,116,964 discloses proteins fused to the amino- or carboxyl-terminal end of an immunoglobulin Fc fragment by genetic recombination. U.S. Pat. No. 5,349,053 discloses a fusion protein comprising IL-2 fused to an immunoglobulin Fc fragment through peptide linkage.

Other examples of Fc fusion proteins prepared by genetic recombination include a fusion protein of interferon-beta or its derivative and an immunoglobulin Fc fragment (International Pat. Publication NO. WO 00/23472), and a fusion protein of IL-5 receptor and an immunoglobulin Fc fragment (U.S. Pat. No. 5,712,121). However, techniques for improving the duration of action for physiologically active polypeptide drugs using an immunoglobulin Fc fragment are mostly focused on using the immunoglobulin Fc fragment only as a fusion partner, and to date, the technique of using an immunoglobulin Fc fragment as a carrier has not been reported.

Techniques involving the modification of amino acid residues of an immunoglobulin Fc fragment are also known. For example, U.S. Pat. No. 5,605,690 discloses a TNFR-IgG1 Fc fusion protein, which is prepared by genetic recombination using an IgG1 Fc fragment having amino acid alterations in the complement binding region or receptor binding region.

However, such Fc fusion proteins produced by genetic recombination have the following disadvantages: protein fusion occurs only in a specific region of an immunoglobulin Fc fragment, which is at an amino- or carboxyl-terminal end; only homodimeric forms and not monomeric forms are produced; and a fusion could take place only between the glycosylated proteins or between the aglycosylated proteins, and it is impossible to make a fusion protein composed of a glycosylated protein and an aglycosylated protein. Further, a new amino acid sequence created by the fusion may trigger immune responses, and a linker region may become susceptible to proteolytic degradation.

To solve these problems, the inventors of the present application conducted a research, and came to a knowledge that, when an IgG Fc fragment, more particularly an IgG2 or IgG4 Fc fragment, is linked to a drug, it could improve the in vivo duration of the drug and minimize a reduction in the in vivo activity.

DISCLOSURE OF THE INVENTION

It is therefore an object of the present invention to provide an immunoglobulin G fragment that is useful as a drug carrier.

It is another object of the present invention to provide a recombinant vector expressing an immunoglobulin G fragment.

It is a further object of the present invention to provide a transformant transformed with a recombinant vector expressing an immunoglobulin G fragment.

It is yet another object of the present invention to provide a method for preparing an immunoglobulin G fragment, comprising culturing a transformant transformed with a recombinant vector expressing the immunoglobulin G fragment.

It is still another object of the present invention to provide a pharmaceutical composition comprising an immunoglobulin G fragment.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
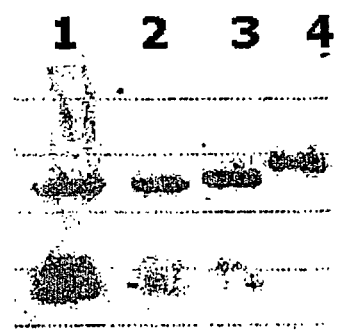
FIG. 1 shows the results of Western blotting of immunoglobulin Fc fragments expressed in E. coli under non-reduced conditions.

In one aspect, the present invention relates to an immunoglobulin G Fc fragment useful as a drug carrier, and more preferably IgG2 Fc and IgG4 Fc fragments.

The term "carrier", as used herein, refers to a substance linked with a drug, which typically increases, decreases or eliminates the physiological activity of the drug by binding to the drug. However, with respect to the objects of the present invention, a carrier is employed in the present invention for minimizing a decrease in the physiological activity of a drug of interest, linked to the carrier, while enhancing the in vivo stability of the drug.

A large number of substances, such as lipids and polymers, were studied to determine their suitability as drug carriers. However, techniques employing an immunoglobulin Fc fragment as a drug carrier are unknown. That is, the present invention is characterized by providing particularly an IgG Fc fragment among various substances available as carriers for improving the in vivo duration of action of a drug to which the carrier is conjugated and minimizing a decrease in the in vivo activity of the drug, and more preferably IgG2 Fc and IgG4 Fc fragments.

The term "immunoglobulin G (hereinafter, used interchangeably with "IgG")", as used herein, collectively means proteins that participate in the body's protective immunity by selectively acting against antigens, and may be derived from humans and animals. Immunoglobulins have the following general structure. Immunoglobulins are composed of two identical light chains and two identical heavy chains. The light and heavy chains comprise variable and constant regions. There are five distinct types of heavy chains based on differences in the amino acid sequences of their constant regions: gamma (γ), mu (μ), alpha (α), delta (δ) and epsilon (ε), and the heavy chains include the following subclasses: gamma 1 (γ1), gamma 2 (γ2), gamma 3 (γ3), gamma 4 (γ4), alpha 1 (α1) and alpha 2 (α2). Also, there are two types of light chains based on differences in the amino acid sequences of their constant regions: kappa (κ) and lambda (λ) types (Coleman et al., Fundamental Immunology, 2nd Ed., 1989, 55-73). According to the features of the constant regions of the heavy chains, immunoglobulins are classified into five isotypes: IgG, IgA, IgD, IgE and IgM. IgG is divided into IgG1, IgG2, IgG3 and IgG4 subclasses.

In addition, immunoglobulins are known to generate several structurally different fragments, which include Fab, F(ab'), F(ab')2, Fv, scFv, Fd and Fc. Among the immunoglobulin fragments, Fab contains the variable regions of the light chain and the heavy chain, the constant region of the light chain and the first constant region ($C_H1$) of the heavy chain, and has a single antigen-binding site. The Fab' fragments differ from the Fab fragments in terms of having the hinge region containing one or more cysteine residues at the C-terminus (carboxyl terminus) of the heavy chain $C_H1$ domain. The F(ab')$_2$ fragments are produced as a pair of the Fab' fragments by disulfide bonding formed between cysteine residues of the hinge regions of the Fab' fragments. Fv is the minimum antibody fragment that contains only the heavy-chain variable region and the light-chain variable region. The scFv (single-chain Fv) fragments comprise both the heavy-chain variable region and the light-chain variable region that are linked to each other by a peptide linker and thus are present in a single polypeptide chain. The Fd fragments comprise only the variable region and $C_H1$ domain of the heavy chain.

Among the known various types of immunoglobulins and their functional and structural fragments, as described above, the present invention is characterized by providing an IgG Fc fragment useful as a drug carrier, and more preferably IgG2 Fc and IgG4 Fc fragments.

The term "immunoglobulin G Fc fragment (hereinafter, used interchangeably with "IgG Fc fragment" or "Fc fragment of the present invention")", as used herein, refers to a protein that contains the heavy-chain constant region 2 ($C_H2$) and the heavy-chain constant region 3 ($C_H3$) of an immunoglobulin G, and not the variable regions of the heavy and light chains, the heavy-chain constant region 1 ($C_H1$) and the light-chain constant region 1 ($C_L1$) of the immunoglobulin G. It may further include the hinge region at the heavy-chain constant region. Also, the IgG Fc fragment of the present invention may contain a portion or the all the heavy-chain constant region 1 ($C_H1$) and/or the light-chain constant region 1 ($C_L1$), except for the variable regions of the heavy and light chains. Also, as long as it has a physiological function substantially similar to or better than the native protein the IgG Fc fragment may be a fragment having a deletion in a relatively long portion of the amino acid sequence of $C_H2$ and/or $C_H3$.

The Fc fragment of the present invention includes a native amino acid sequence and sequence derivatives (mutants) thereof. An amino acid sequence derivative is a sequence that is different from the native amino acid sequence due to a deletion, an insertion, a non-conservative or conservative substitution or combinations thereof of one or more amino acid residues. For example, in an IgG Fc, amino acid residues known to be important in binding, at positions 214 to 238, 297 to 299, 318 to 322, or 327 to 331, may be used as a suitable target for modification. Also, other various derivatives are possible, including one in which a region capable of forming a disulfide bond is deleted, or certain amino acid residues are eliminated at the N-terminal end of a native Fc form or a methionine residue is added thereto. Further, to remove effector functions, a deletion may occur in a complement-binding site, such as a C1q-binding site and an ADCC site. Techniques of preparing such sequence derivatives of the immunoglobulin Fc fragment are disclosed in International Pat. Publication Nos. WO 97/34631 and WO 96/32478.

Amino acid exchanges in proteins and peptides, which do not generally alter the activity of the proteins, or peptides are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions.

In addition, the Fc fragment, if desired, may be modified by phosphorylation, sulfation, acrylation, glycosylation, methylation, farnesylation, acetylation, amidation, and the like.

The aforementioned Fc derivatives are derivatives that have a biological activity identical to the Fc fragment of the present invention or improved structural stability, for example, against heat, pH, or the like.

In addition, these Fc fragments may be obtained from native forms isolated from humans and other animals including cows, goats, swine, mice, rabbits, hamsters, rats and guinea pigs, or may be recombinants or derivatives thereof, obtained from transformed animal cells or microorganisms. Herein, they may be obtained from a native immunoglobulin by isolating whole immunoglobulins from human or, animal organisms and treating them with a proteolytic enzyme. Papain digests the native immunoglobulin into Fab and Fc fragments, and pepsin treatment results in the production of pF'c and F(ab') 2 fragments. These fragments may be subjected, for example, to size exclusion chromatography to isolate Fc or pF'c. Preferably, a human-derived Fc fragment is a recombinant IgG Fc fragment that is obtained from a microorganism. That is, preferred are human-derived recombinant IgG2 Fc and IgG4 Fc fragments obtained from a microorganism.

In addition, the Fc fragment of the present invention may be in the form of having native sugar chains, increased sugar chains compared to a native form or decreased sugar chains compared to the native form, or may be in a deglycosylated form. The increase, decrease or removal of sugar chains of the Fc fragment may be achieved by methods common in the art, such as a chemical method, an enzymatic method and a genetic engineering method using a microorganism. The removal of sugar chains from an Fc fragment results in a sharp decrease in binding affinity to the C1q part of the first complement component C1 and a decrease or loss in antibody-dependent cell-mediated cytotoxicity (ADCC) or complement-dependent cytotoxicity (CDC), thereby not inducing unnecessary immune responses in vivo. In this regard, an immunoglobulin Fc fragment in a deglycosylated or aglycosylated form may be more suitable to the object of the present invention as a drug carrier.

Figure 18:
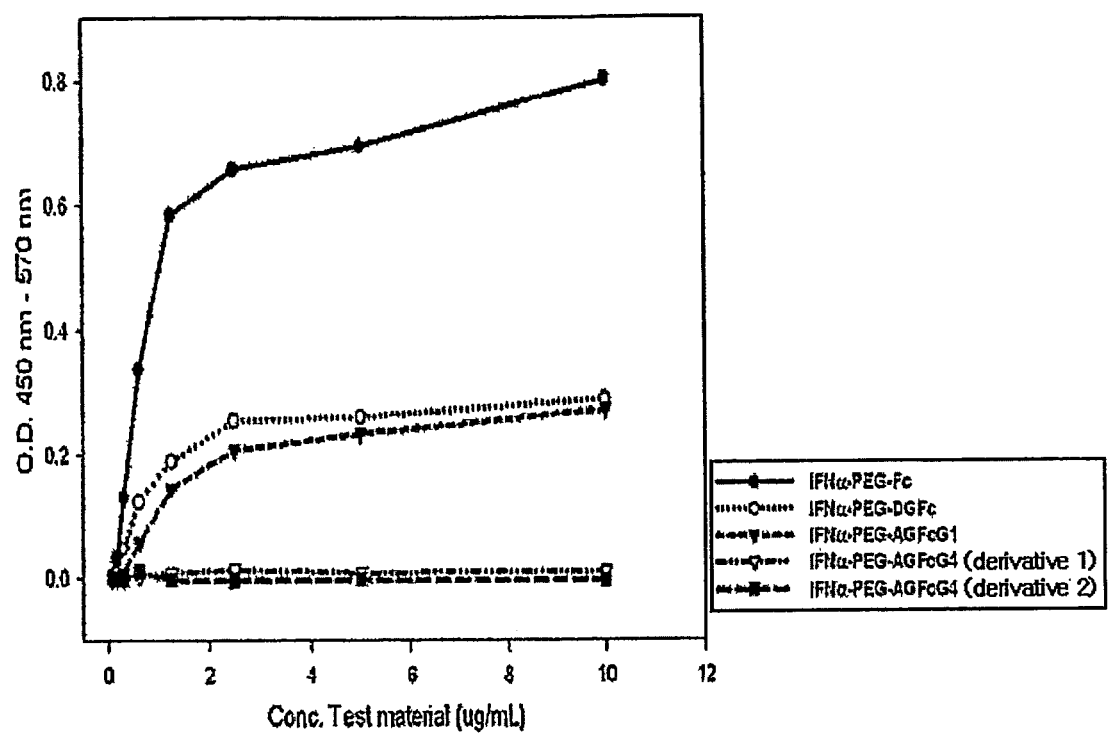
FIG. 18 is a graph showing the results of comparison of a glycosylated Fc, an enzymatically deglycosylated DG Fc and an interferon-PEG-carrier conjugate where the carrier is AG Fc produced by E. coli for binding affinity to the C1q complement.

As apparent in FIG. 18, a glycosylated Fc has stronger CDC activity than an aglycosylated Fc and thus has a high risk of inducing immune responses. Thus, with the objects of the present invention, preferred is an aglycosylated or deglycosylated Fc fragment. More preferred are aglycosylated IgG2 Fc and IgG4 Fc fragments, combinations thereof and hybrids thereof.

As used herein, the term "deglycosylation" refers to that sugar moieties are enzymatically removed from an Fc fragment, and the term "aglycosylation" means that an Fc fragment is produced in an unglycosylated form by a prokaryote, preferably $E.\ coli$.

On the other hand, the term "combination", as used herein, means that polypeptides encoding single-chain immunoglobulin Fc fragments of the same origin are linked to a single-chain polypeptide of a different origin to form a dimer or multimer. That is, a dimer or multimer may be formed from two or more fragments selected from the group consisting of IgG1 Fc, IgG2 Fc, IgG3 Fc and IgG4 Fc fragments.

The term "hybrid", as used herein, means that sequences encoding two or more immunoglobulin Fc fragments of different origin are present in a single-chain immunoglobulin Fc fragment. In the present invention, various types of hybrids are possible. That is, domain hybrids may be composed of one to four domains selected from the group consisting of CH1, CH2, CH3 and CH4 of IgG1 Fc, IgG2 Fc, IgG3 Fc and IgG4 Fc, and may include the hinge region.

Figure 17:
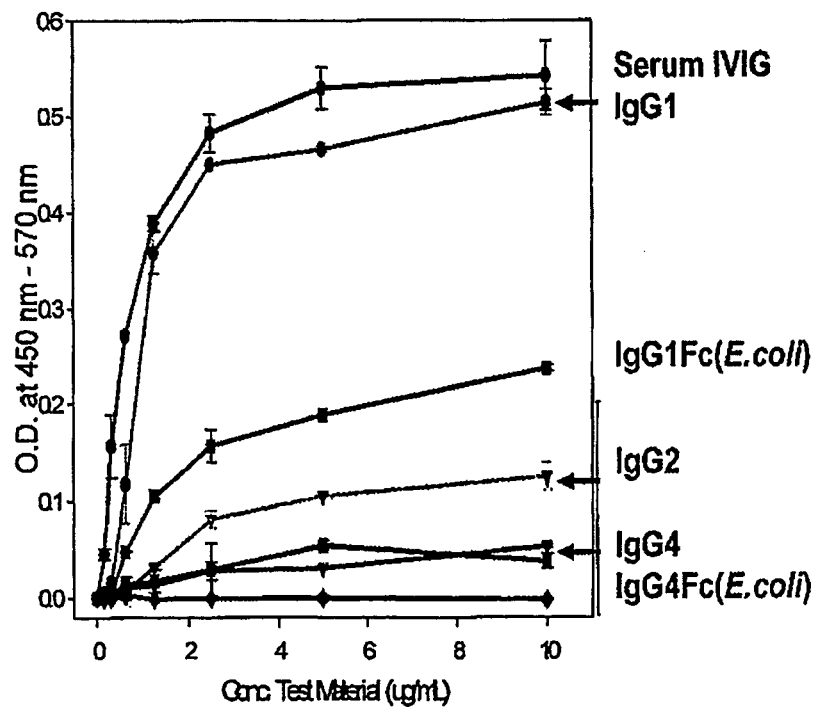
FIG. 17 is a graph showing the results of comparison of human IgG subclasses for binding affinity to the C1q complement.

On the other hand, as shown in the accompanying drawings of the present invention, FIGS. 17 and 18, among several subclasses of IgG, IgG4 has the lowest binding affinity to complement C1q. The decrease in binding affinity to the complement results in a decrease in or removal of antibody-dependent cell-mediated cytotoxicity (ADCC) and complement-dependent cytotoxicity (CDC), and thus, unnecessary immune responses are not induced in vivo. IgG2 and IgG4 Fc fragments have weaker binding affinity to C1q than IgG1, and the IgG4 Fc fragment has the weakest activity. Therefore, since, to be used as a drug carrier, the Fc fragment linked to a drug preferably has weaker effector function activities such as ADCC and CDC, with respect to the objects of the present invention, preferred are IgG2 Fc and IgG4 Fc fragments, more preferred is the IgG4 Fc fragment, and most preferred are Fc fragments having the amino acid sequences of SEQ ID Nos. 8, 10 and 23.

In another aspect, the present invention relates to a gene encoding an IgG Fc fragment, preferably genes encoding IgG2 Fc and IgG4 Fc fragments, and more preferably genes encoding the amino acid sequences of SEQ ID Nos. 8, 10 and 23. Such a gene encoding the Fc of the present invention includes a native nucleotide sequence and sequence derivatives thereof. A nucleotide sequence derivative means to have a sequence different by a deletion, an insertion, a non-conservative or conservative substitution in one or more nucleotide residues of a native nucleotide sequence, or combinations thereof.

In the present invention, a gene encoding an Fc fragment having the amino acid sequence of SEQ ID No. 8 is preferably a gene having the nucleotide sequence of SEQ ID No. 4. A gene encoding an Fc fragment having the amino acid sequence of SEQ ID No. 10 is preferably a gene having the nucleotide sequence of SEQ ID No. 9. A gene encoding an Fc fragment having the amino acid sequence of SEQ ID No. 23 is preferably a gene having the nucleotide sequence of SEQ ID No. 22. The nucleotide sequences encoding the Fc fragments of the present invention may be altered by a substitution, a deletion or an insertion of one more bases, or combinations thereof. The nucleotide sequences may be naturally isolated or artificially synthesized, or may be prepared by a genetic recombination method.

The nucleotide sequences encoding the Fc fragments of the present invention are provided by vectors expressing the same.

In a further aspect, the present invention provides a recombinant vector comprising an IgG Fc fragment.

The term "vector", as used herein, means a vehicle for introducing a DNA molecule into a host cell to express an antibody or an antibody fragment. The vector useful in the present invention includes plasmid vectors, cosmid vectors, bacteriophage vectors, and viral vectors such as adenovirus vectors, retrovirus vectors and adeno-associated virus vectors. The plasmid vector is preferable. With respect to the objects of the present invention, an expression vector may include expression regulatory elements, such as a promoter, an initiation codon, a stop codon, a polyadenylation signal and an enhancer, and a signal sequence for membrane targeting or secretion.

The term "signal sequence", as used herein, refers to a specific amino acid sequence that allows transport and secretion of a protein to the outside of the cytosol. Various types of these signal sequences are known in the art, but, since the present invention preferably uses $E.\ coli$ as a host cell, the signal sequence of the present invention is preferably an $E.\ coli$-derived signal sequence, which an $E.\ coli$ secretory protein possesses. Examples of $E.\ coli$-derived signal sequences include alkaline phosphatase, penicillinase, Ipp, heat-stable enterotoxin II, LamB, PhoE, Pe1B, OmpA and maltose binding protein. Most preferred is heat-stable enterotoxin II.

On the other hand, the initiation and stop codons are generally considered to be a portion of a nucleotide sequence coding for an immunogenic target protein, are necessary to be functional in an individual to whom a genetic construct has been administered, and must be in frame with the coding sequence. Promoters may be generally constitutive or inducible. Non-limiting examples of promoters available in prokaryotic cells include lac, tac, T3 and T7 promoters. Non-limiting examples of promoters available in eukaryotic cells include simian virus 40 (SV40) promoter, mouse mammary tumor virus (MMTV) promoter, human immunodeficiency virus (HIV) promoter such as the HIV Long Terminal Repeat (LTR) promoter, moloney virus promoter, cytomegalovirus (CMV) promoter, epstein barr virus (EBV) promoter, rous sarcoma virus (RSV) promoter, as well as promoters from human genes such as human β-actin, human hemoglobin, human muscle creatine and human metalothionein. In addition, expression vectors include a selectable marker that allows selection of host cells containing the vector, and replicable expression vectors include a replication origin. Genes coding for products that confer resistance to antibiotics or drugs are used as general selectable markers. β-latamase gene (ampicillin resistance) and Tet gene (tetracycline resistance) may be used in prokaryotic cells, and neomycin (G418 or Geneticin), gpt (mycophenolic acid), ampicillin and hygromycin resistant genes may be used in eukaryotic cells. Dihydropholate reductase marker gene may be selected by methotrexate in a variety of hosts. Genes coding for gene products of auxotrophic markers of hosts, for example, LEU2, URA3 and HIS3, are often used as selectable markers in yeasts. Also, available are viruses (e.g., vaculovirus) or phage vectors, and vectors that are able to integrate into the genome of host cells, such as retrovirus vectors.

To prepare an IgG Fc fragment that coincide with the objects of the present invention, a vector is used, which carries a gene coding for the amino acid sequence of SEQ ID No. 8, 10 or 23. In the present invention, using pT14S1SH-4T20V22Q (Korean Pat. No. 38061) as a starting vector, the following two vectors are constructed: pSTIIdCG2Fc that carries a gene designated as SEQ ID No. 22 encoding the amino acid sequence of SEQ ID No. 23, and pSTIIdCG4Fc that carries a gene designated as SEQ ID No. 4 encoding the amino acid sequence of SEQ ID No. 8. Also, by performing PCR using the pSTIIdCG4Fc plasmid, a gene designated as SEQ ID No. 9 encoding the amino acid sequence of SEQ ID No. 10 is obtained, the gene having a deletion in the hinge region required for dimer formation from a gene amplified by the PCR, and a pSTIIG4Mo vector carrying the gene is then constructed.

In yet another aspect, the present invention relates to a transformant transformed with the recombinant vector.

Since expression levels and modification of proteins vary depending on host cells, the most suitable host cell may be selected according to the intended use. Available host cells include, but are not limited to, prokaryotic cells such as *Escherichia coli, Bacillus subtilis, Streptomyces, Pseudomonas, Proteus mirabilis* or *Staphylococcus*. In addition, useful as host cells are lower eukaryotic cells, such as fungi (e.g., *Aspergillus*) and yeasts (e.g., *Pichia pastoris, Saccharomyces cerevisiae, Schizosaccharomyces, Neurospora crassa*), insect cells, plant cells, and cells derived from higher eukaryotes including mammals. However, since the immunoglobulin Fc fragment is advantageously in an aglycosylated form with respect to the objects of the present invention, the prokaryotic host cells are preferable, and in particular, *E. coli* is most preferable.

In the present invention, "transformation" and/or "transfection" into host cells includes any methods by which nucleic acids can be introduced into organisms, cells, tissues or organs, and, as known in the art, may be performed by selecting suitable standard techniques according to host cells. These methods include, but are not limited to, electroporation, protoplast fusion, calcium phosphate ($CaPO_4$) precipitation, calcium chloride ($CaCl_2$) precipitation, and agitation with silicon carbide fiber, *agrobacterium*-mediated transformation, and PEG-, dextran sulfate-, lipofectamine- and desiccation/inhibition-mediated transformation. For example, calcium treatment using calcium chloride or electroporation is generally used in prokaryotic cells (Sambrook et al., 1989, Molecular Cloning: A Laboratory Manual (New York: Cold Spring Harbor Laboratory Press)). Transfection using *Agrobacterium tumefaciens* is used for transformation of specific plant cells (Shaw et al., 1983, Gene, 23:315; International Pat. Publication No. WO 89/05859). For mammalian cells having no cell walls, calcium phosphate precipitation may be used (Graham et al, 1978, Virology, 52:456-457). The generally methods and features of transformation into mammalian host cells are described in U.S. Pat. No. 4,399,216. Transformation into yeasts is typically carried out according to the methods described by Van Solingen et al., J. Bact., 1977, 130:946, and Hsiao et al., Proc. Natl. Acad. Sci. (USA), 1979, 76:3829.

The expression vectors according to the present invention are transformed into host cells, and the resulting transformants of the present invention are designated as HM10932 (pSTIIdCG4Fc-introduced transformant), HM10933 (pSTIIG4Mo-introduced transformant) and HM10936 (pSTIIdCG2Fc-introduced transformant).

In still another aspect, the present invention provides a method of preparing an immunoglobulin fragment, comprising culturing a transformant transformed with a vector capable of expressing an IgG Fc fragment, and preferably IgG2 Fc or IgG4 Fc fragment, or a combination thereof or a hybrid thereof, under suitable conditions.

In the method of preparing the immunoglobulin fragment, the culturing of transformant may be performed using suitable media under suitable culture conditions, which are known in the art. This culturing process may be easily adjusted according to the strains selected by those skilled in the art.

The immunoglobulin fragment of the present invention, obtained by culturing the transformant, may be used in an unpurified form, or may be used after being purified with high purities using various general methods, for example, dialysis, salt precipitation and chromatography. Among them, chromatography is most commonly used. As no rule is applicable to any case in selecting the type and sequence of used columns, chromatography may be selected according to the properties and culture method of target proteins of antibodies, for example, from ion exchange chromatography, size exclusion chromatography, affinity chromatography and protein-A affinity column chromatography. In preferred embodiments of the present invention, the immunoglobulin fragment is purified using a protein-A affinity column, a SP sepharose FF column, and the like.

When the Fc fragment thus obtained is in the free form, it may be converted into a salt form by a per se known method or a modified method. In contrast, when it is obtained in a salt form, the salt may be converted into the free form or another salt by a per se known method or a modified method. Also, the Fc fragment as produced by a transformant may be treated before or after purification with an appropriate protein-modifying enzyme for arbitrary modification or partial polypeptide removal. Examples of the protein-modifying enzyme useful in the present invention include trypsin, chymotrypsin, arginine endopeptidase, protein kinase and glycosidase.

The Fc fragment of the present invention, prepared as described above, acts as a drug carrier and forms a conjugate with a drug.

The term "drug conjugate" or "conjugate", as used herein, means that one or more drugs are linked with one or more immunoglobulin Fc fragments.

The term "drug", as used herein, refers to a substance displaying therapeutic activity when administered to humans or animals, and examples of the drug include, but are not limited to, polypeptides, compounds, extracts and nucleic acids. Preferred is a polypeptide drug.

The terms "physiologically active polypeptide", "physiologically active protein", "active polypeptide" "polypeptide drug" and "protein drug", as used herein, are interchangeable in their meanings, and are featured in that they are in a physiologically active form exhibiting various in vivo physiological functions.

The polypeptide drug has a disadvantage of being unable to sustain physiological action for a long period of time due to its property of being easily denatured or degraded by proteolytic enzymes present in the body. However, when the polypeptide drug is conjugated to the immunoglobulin Fc fragment of the present invention to form a conjugate, the drug has increased structural stability and degradation half-life. Also, the polypeptide conjugated to the Fc fragment has a much smaller decrease in physiological activity than other known polypeptide drug formulations. Therefore, compared to the in vivo bioavailability of conventional polypeptide drugs, the conjugate of the polypeptide and the Fc fragment according to the present invention is characterized by having markedly improved in vivo bioavailability. This is also clearly described through embodiments of the present invention. That is, when linked to the Fc fragment of the present invention, IFNα, G-CSF, hGH and other protein drugs displayed an about two- to six-fold increase in vivo bioavailability compared to their conventional forms conjugated to PEG alone or both PEG and albumin (Tables 8, 9 and 10).

On the other hand, the linkage of a protein and the Fc fragment of the present invention is featured in that it is not a fusion by a conventional recombination method. A fusion form of the immunoglobulin Fc fragment and an active polypeptide used as a drug by a recombination method is obtained in such a way that the polypeptide is linked to the N-terminus or C-terminus of the Fc fragment, and is thus expressed and folded as a single polypeptide from a nucleotide sequence encoding the fusion form.

This brings about a sharp decrease in the activity of the resulting fusion protein because the activity of a protein as a physiologically functional substance is determined by the conformation of the protein. Thus, when a polypeptide drug is fused with Fc by a recombination method, there is no effect with regard to in vivo bioavailability even when the fusion protein has increased structural stability. Also, since such a fusion protein is often misfolded and thus expressed as inclusion bodies, the fusion method is uneconomical in protein production and isolation yield. Further, when the active form of a polypeptide is in a glycosylated form, the polypeptide should be expressed in eukaryotic cells. In this case, Fc is also glycosylated, and this glycosylation may cause unsuitable immune responses in vivo.

That is, only the present invention makes it possible to produce a conjugate of a glycosylated active polypeptide and an aglycosylated immunoglobulin Fc fragment, and overcomes all of the above problems, including improving protein production yield, because the two components of the complex are individually prepared and isolated by the best systems.

Non-limiting examples of protein drugs capable of being conjugated to the immunoglobulin Fc fragment of the present invention include human growth hormone, growth hormone releasing hormone, growth hormone releasing peptide, interferons and interferon receptors (e.g., interferon-α, -β and -γ, water-soluble type I interferon receptor, etc.), granulocyte colony stimulating factor (G-CSF), granulocyte-macrophage colony stimulating factor (GM-CSF), glucagon-like peptides (e.g., GLP-1, etc.), G-protein-coupled receptor, interleukins (e.g., IL-1 receptor, IL-4 receptor, etc.), enzymes (e.g., glucocerebrosidase, iduronate-2-sulfatase, alpha-galactosidase-A, agalsidase alpha and beta, alpha-L-iduronidase, butyrylcholinesterase, chitinase, glutamate decarboxylase, imiglucerase, lipase, uricase, platelet-activating factor acetylhydrolase, neutral endopeptidase, myeloperoxidase, etc.), interleukin and cytokine binding proteins (e.g., IL-18 bp, TNF-binding protein, etc.), macrophage activating factor, macrophage peptide, B cell factor, T cell factor, protein A, allergy inhibitor, cell necrosis glycoproteins, immunotoxin, lymphotoxin, tumor necrosis factor, tumor suppressors, metastasis growth factor, alpha-1 antitrypsin, albumin, alpha-lactalbumin, apolipoprotein-E, erythropoietin, highly glycosylated erythropoietin, angiopoietins, hemoglobin, thrombin, thrombin receptor activating peptide, thrombomodulin, factor VII, factor VIIa, factor VIII, factor IX, factor XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors (e.g., nerve growth factor, ciliary neurotrophic factor, axogenesis factor-1, brain-natriuretic peptide, glial derived neurotrophic factor, netrin, neurophil inhibitor factor, neurotrophic factor, neuturin, etc.), parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, receptors (e.g., TNFR(P75), TNFR(P55), IL-1 receptor, VEGF receptor, B cell activating factor receptor, etc.), receptor antagonists (e.g., IL1-Ra etc.), cell surface antigens (e.g., CD 2, 3, 4, 5, 7, 11a, 11b, 18, 19, 20, 23, 25, 33, 38, 40, 45, 69, etc.), monoclonal antibodies, polyclonal antibodies, antibody fragments (e.g., scFv, Fab, Fab', F(ab')2 and Fd), and virus derived vaccine antigens. An antibody fragment may be Fab, Fab', F(ab')2, Fd or scFv, which is capable of binding to a specific antigen, and preferably Fab'.

In particular, preferred as physiologically active polypeptides are those requiring frequent dosing upon administration to the body for therapy or prevention of diseases, which include human growth hormone, interferons (interferon-α, -β, -γ, etc.), granulocyte colony stimulating factor, erythropoietin (EPO) and antibody fragments. In addition, certain derivatives are included in the scope of the physiologically active polypeptides of the present invention as long as they have function, structure, activity or stability substantially identical to or improved compared over native forms of the physiologically active polypeptides. In the present invention, the most preferable polypeptide drug is interferon-alpha.

In addition to the polypeptide drugs, other drugs are also available in the present invention. Non-limiting examples of these drugs include antibiotics selected from among derivatives and mixtures of tetracycline, minocycline, doxycycline, ofloxacin, levofloxacin, ciprofloxacin, clarithromycin, erythromycin, cefaclor, cefotaxime, imipenem, penicillin, gentamycin, streptomycin, vancomycin, and the like; anticancer agents selected from among derivatives and mixtures of methotrexate, carboplatin, taxol, cisplatin, 5-fluorouracil, doxorubicin, etoposide, paclitaxel, camtotecin, cytosine arabinoside, and the like; anti-inflammatory agents selected from among derivatives and mixtures of indomethacin, ibuprofen, ketoprofen, piroxicam, probiprofen, diclofenac, and the like; antiviral agents selected from among derivatives and mixtures of acyclovir and robavin; and antibacterial agents selected from among derivatives and mixtures of ketoconazole, itraconazole, fluconazole, amphotericin B and griseofulvin.

On the other hand, the Fc fragment of the present invention is able to form a conjugate linked to a drug through a linker.

This linker includes peptide and non-peptide linkers. Preferred is a non-peptide linker, and more preferred is a non-peptide polymer. The peptide linker means amino acids, and preferably 1 to 20 amino acids, which are linearly linked to each other by peptide bonding, and may be in a glycosylated form. This peptide linker is preferably a peptide having a repeating unit of Gly and Ser, which is immunologically inactive for T cells. Examples of the non-peptide polymer include poly(ethylene glycol), poly (propylene glycol), copolymers of ethylene glycol and propylene glycol, polyoxyethylated polyols, polyvinyl alcohol, polysaccharides, dextran, polyvinyl ether, biodegradable polymers such as PLA (poly (lactic acid) and PLGA (poly (lactic-glycolic acid)), lipid polymers, chitins, and hyaluronic acid. Most preferred is poly (ethylene glycol) (PEG).

The conjugate of the present invention, Fc fragment-drug or Fc fragment-linker-drug, is made at various molar ratios. That is, the number of the Fc fragment and/or linker linked to a single polypeptide drug is not limited. However, preferably, in the drug conjugate of the present invention, the drug and the Fc fragment are conjugated to each other at a molar ratio of 1:1 to 10:1, and preferably 1:1 to 2:1.

In addition, the linkage of the Fc fragment of the present invention, a certain linker and a certain drug include all covalent bonds except for a peptide bond formed when the Fc fragment and a polypeptide drug are expressed as a fusion protein by genetic recombination, and all types of non-covalent bonds such as hydrogen bonds, ionic interactions, van der Waals forces and hydrophobic interactions. However, with respect to the physiological activity of the drug, the linkage is preferably made by covalent bonds.

In addition, the Fc fragment of the present invention, a certain linker and a certain drug may be linked to each other at a certain site of the drug. On the other hand, the Fc fragment of the present invention and a polypeptide drug may be linked to each other at an N-terminus or C-terminus, and preferably at a free group, and a covalent bond between the Fc fragment and the drug is easily formed especially at an amino terminal end, an amino group of a lysine residue, an amino group of a histidine residue, or a free cysteine residue.

On the other hand, the linkage of the Fc fragment of the present invention, a certain linker and a certain drug may be made in a certain direction. That is, the linker may be linked to the N-terminus, the C-terminus or a free group of the immunoglobulin Fc fragment, and may also be linked to the N-terminus, the C-terminus or a free group of the protein drug. When the linker is a peptide linker, the linkage may take place at a certain linking site.

Also, the conjugate of the present invention may be prepared using any of a number of coupling agents known in the art. Non-limiting examples of the coupling agents include 1,1-bis(diazoacetyl)-2-phenylethane, glutaradehyde, N-hydroxysuccinimide esters such as esters with 4-azidosalicylic acid, imidoesters including disuccinimidyl esters such as 3,3'-dithiobis (succinimidylpropionate), and bifunctional maleimides such as bis-N-maleimido-1,8-octane.

On the other hand, the conjugate of the novel Fc fragment of the present invention and a drug may offer a various number of pharmaceutical compositions.

The term "administration", as used herein, means introduction of a predetermined amount of a substance into a patient by a certain suitable method. The conjugate of the present invention may be administered via any of the common routes, as long as it is able to reach a desired tissue. A variety of modes of administration are contemplated, including intraperitoneally, intravenously, intramuscularly, subcutaneously, intradermally, orally, topically, intranasally, intrapulmonarily and intrarectally, but the present invention is not limited to these exemplified modes of administration. However, since peptides are digested upon oral administration, active ingredients of a composition for oral administration should be coated or formulated for protection against degradation in the stomach. Preferably, the present composition may be administered in an injectable form. In addition, the pharmaceutical composition of the present invention may be administered using a certain apparatus capable of transporting the active ingredients into a target cell.

The pharmaceutical composition comprising the conjugate according to the present invention may include a pharmaceutically acceptable carrier. For oral administration, the pharmaceutically acceptable carrier may include binders, lubricants, disintegrators, excipients, solubilizers, dispersing agents, stabilizers, suspending agents, coloring agents and perfumes. For injectable preparations, the pharmaceutically acceptable carrier may include buffering agents, preserving agents, analgesics, solubilizers, isotonic agents and stabilizers. For preparations for topical administration, the pharmaceutically acceptable carrier may include bases, excipients, lubricants and preserving agents. The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into a unit dosage form, such as a multidose container or an ampule as a single-dose dosage form. The pharmaceutical composition may be also formulated into solutions, suspensions, tablets, capsules and long-acting preparations.

On the other hand, examples of carriers, exipients and diluents suitable for the pharmaceutical formulations include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, perfumes, emulsifiers and antiseptics.

A substantial dosage of a drug in combination with the Fc fragment of the present invention as a carrier may be determined by several related factors including the types of diseases to be treated, administration routes, the patient's age, gender, weight and severity of the illness, as well as by the types of the drug as an active component. Since the pharmaceutical composition of the present invention has a very long duration of action in vivo, it has an advantage of greatly reducing administration frequency of pharmaceutical drugs.

A better understanding of the present invention may be obtained through the following examples which are set forth to illustrate, but are not to be construed as the limit of the present invention.

EXAMPLES

Preparation of Immunoglobulin Fc Fragments

Example 1

Construction of Human Immunoglobulin IgG4 Fc Expression Vector

<1-1> Construction of Dimeric IgG4 Fc Expression Vector

To clone a gene encoding the Fc region of human immunoglobulin IgG4, RT-PCR was carried out using RNA isolated from human blood cells as a template, as follows. First, total RNA was isolated from about 6 ml of blood using a Qiamp RNA blood kit (Qiagen), and gene amplification was performed using the total RNA as a template and a One-Step RT-PCR kit (Qiagen). To obtain a desired gene sequence, a pair of primers represented by SEQ ID Nos. 1 and 2 was used. SEQ ID No. 1 is a nucleotide sequence starting from the 10th residue, serine, of 12 amino acid residues of the hinge region of IgG4 (Glu Ser Lys Tyr Gly Pro Pro Cys Pro Ser Cys Pro: SEQ ID No. 3). SEQ ID No. 2 was designed to have a BamHI recognition site containing a stop codon. The gene amplified using the primer set was identified to have the nucleotide sequence represented by SEQ ID No. 4 and contain an amino terminal end, starting with the Ser-Cys-Pro sequence of the hinge region of a full-length IgG4 Fc gene sequence, and CH2 and CH3 domains. To clone the amplified IgG4 Fc gene fragment into an expression vector containing an *E. coli* signal sequence, an expression vector pT14S1SH-4T20V22Q (Korean Pat. No. 38061), previously developed by the present inventors, was used as a starting vector. This expression vector contains an *E. coli* heat-stable enterotoxin signal sequence derivative having the nucleotide sequence represented by SEQ ID No. 5. To facilitate cloning, a StuI recognition site was inserted into an end of the *E. coli* heat-stable enterotoxin signal sequence derivative of the pT14S1SH-4T20V22Q plasmid through site-directed mutagenesis using a pair of primers represented by SEQ ID Nos. 6 and 7 to induce mutagenesis to introduce the StuI site at a nucleotide sequence coding for the last amino acid residue of the signal sequence. This insertion of the StuI site was identified to be successful by DNA sequencing. The resulting pT14S1SH-4T20V22Q plasmid containing a StuI site was designated as "pmSTII". The pmSTII plasmid was treated with StuI and BamHI and subjected to agarose gel electrophoresis, and a large fragment (4.7 kb), which contained the *E. coli* heat-stable enterotoxin signal sequence derivative, was purified. Then, the amplified IgG4 Fc gene fragment was digested with BamHI and ligated with the linearized expression vector, thus providing a pSTIIdCG4Fc plasmid. This vector expresses a protein that has the amino acid sequence of SEQ ID No. 8 and is present in a dimeric form by disulfide bonds between cysteine residues in the hinge region. The final expression vector was transformed into *E. coli* BL21 (DE3), and the resulting transformant was designated as "BL21/pSTIIdCG4Fc (HM10932)", which was deposited at the Korean Culture Center of Microorganisms (KCCM) on Sep. 15, 2004 and assigned accession number KCCM-10597.

<1-2> Construction of Monomeric IgG4 Fc Expression Vector

To clone an IgG4 Fc fragment to be expressed in a monomeric form, PCR was carried out using a pair of primers represented by SEQ ID Nos. 9 and 2 and the pSTIIdCG4Fc plasmid prepared in the above <1-1> as a template. To allow an amplified gene to be expressed in a monomeric form, the PCR was designed for a PCR product to have a deletion in the hinge region required for dimer formation from the IgG4 Fc sequence, and thus, only the CH2 and CH3 domains of IgG4 Fc were amplified. The PCR product was cloned into an expression vector, pmSTII, according to the same procedure as in the above <1-1>, thus providing a pSTIIG4Mo plasmid. This expression vector was transformed into *E. coli* BL21 (DE3), and the resulting transformant was designated as "BL21/pSTIIG4Mo (HM10933)", which was deposited at the Korean Culture Center of Microorganisms (KCCM) on Sep. 15, 2004 and assigned accession number KCCM-10598. A protein expressed by the expression vector has the amino acid sequence of SEQ ID No. 10, and is expressed from the CH2 domain and present in a monomeric form because it has no hinge region.

Example 2

Construction of Human Immunoglobulin IgG1 Fc Expression Vector

<2-1> Construction of Dimeric IgG1 Fc Expression Vector

To clone a gene encoding the Fc region of human IgG1, RT-PCR was carried out according to the same method as in the <1-1> of Example 1 using RNA isolated from human blood cells as a template using a One-Step RT-PCR kit (Qiagen). To obtain a desired gene sequence, a pair of primers represented by SEQ ID Nos. 11 and 12 was used.

SEQ ID No. 11 is a nucleotide sequence starting from the 13th residue, proline, of 15 amino acid residues of the hinge region (Glu Pro Lys Ser Cys Asp Lys Thr His Thr Cys Pro Pro Cys Pro: SEQ ID No. 13).

The gene amplified using the pair of primers represented by SEQ ID Nos. 11 and 12 was found to contain an amino terminal end starting with the Pro-Cys-Pro sequence of the hinge region and CH2 and CH3 domains, among a full-length IgG1 Fc gene sequence, and has the nucleotide sequence of SEQ ID No. 14.

To clone the amplified IgG1 Fc gene into an expression vector containing an *E. coli* signal sequence, the aforementioned pmSTII vector was used. According to a similar cloning procedure to that in the <1-1> of Example 1, the pmSTII plasmid was treated with StuI and BamHI and subjected to agarose gel electrophoresis, and a large fragment (4.7 kb), which contained the *E. coli* heat-stable enterotoxin signal sequence derivative, was purified. Then, the amplified IgG1 Fc gene was digested with BamHI and ligated with the linearized expression vector, thus providing pSTIIdCG1Fc. This vector expresses in a host cell a protein that has the amino acid sequence of SEQ ID No. 15 and is present in a dimeric form by disulfide bonds between cysteine residues in the hinge region. The final expression vector was transformed into *E. coli* BL21 (DE3), and the resulting transformant was designated as "BL21/pSTIIdCG1Fc (HM10927)", which was deposited at the Korean Culture Center of Microorganisms (KCCM) on Sep. 15, 2004 and assigned accession number KCCM-10588.

<2-2> Construction of Monomeric IgG1 Fc Expression Vector

To prepare an IgG1 Fc fragment to be expressed in a monomeric form, PCR was carried out using a pair of primers represented by SEQ ID Nos. 16 and 12 and the pSTIIdCG1Fc plasmid prepared in the <2-1> of Example 2 as a template. The PCR product was cloned into an expression vector, pmSTII, according to the same procedure as in the <2-1> of Example 2, thus providing a pSTIIG1Mo plasmid containing the nucleotide sequence represented by SEQ ID No. 17. This expression vector was transformed into *E. coli* BL21 (DE3), and the resulting transformant was designated as "BL21/pSTIIG1Mo (HM10930)", which was deposited at the Korean Culture Center of Microorganisms (KCCM) on Sep. 15, 2004 and assigned accession number KCCM-10595. A protein expressed by the expression vector is expressed from the CH2 domain and presents in a monomeric form because it was deleted from the hinge region containing cysteine residues allowing dimer formation, and has the amino acid sequence of SEQ ID No. 18.

Example 3

Construction of Human Immunoglobulin IgG2 Fc Expression Vector

To clone a gene encoding the Fc region of human IgG2, RT-PCR was carried out according to the same method as in the <1-1> of Example 1 using RNA isolated from human blood cells as a template using a One-Step RT-PCR kit (Qiagen). To obtain a desired gene sequence, a pair of primers represented by SEQ ID Nos. 19 and 20 was used. SEQ ID No. 19 is a nucleotide sequence starting from the 10th residue, proline, of 12 amino acid residues of the hinge region (Glu Arg Lys Cys Cys Val Glu Cys Pro Pro Cys Pro: SEQ ID No. 21). The gene amplified using the pair of primers represented by SEQ ID Nos. 19 and 20 was identified to contain an amino terminal end, starting with the Pro-Cys-Pro sequence of the hinge region of a full-length IgG2 Fc gene sequence, and CH2 and CH3 domains, and has the nucleotide sequence of SEQ ID No. 22. To clone the amplified IgG2 Fc gene fragment into an expression vector containing an *E. coli* signal sequence, the aforementioned pmSTII vector was used. According to a similar cloning procedure to that in the <1-1> of Example 1, the pmSTII plasmid was treated with StuI and BamHI and subjected to agarose gel electrophoresis, and a large fragment (4.7 kb), which contained the *E. coli* heat-stable enterotoxin signal sequence derivative, was purified. Then, the amplified IgG1 Fc gene fragment was digested with BamHI and ligated with the linearized expression vector fragment, thus providing pSTIIdCG2Fc. This vector expresses in a host cell a protein that has the amino acid sequence of SEQ ID No. 23 and is present in a dimeric form by disulfide bonds between cysteine residues in the hinge region. The final expression vector was transformed into *E. coli* BL21 (DE3), and the resulting transformant was designated as BL21/pSTIIdCG2Fc (HM10936).

Example 4

Expression and Purification of Immunoglobulin Fc

<4-1> Evaluation of Expression of Immunoglobulin Fc

Bacterial transformants prepared in Examples 1, 2 and 3 were individually inoculated in a fermentor (Marubishi Company) and allowed to ferment, and were evaluated to determine whether they express immunoglobulin Fc fragments.

First, each transformant was grown in 100 ml of LB medium with agitation overnight and inoculated in the fermentor for large-scale culture. The fermentor was maintained at 30° C. or 35° C. To prevent conversion from an aerobic to an anaerobic environment, the cultures were aerated with 20-vvm air and stirred at 500 rpm. To compensate for the insufficient nutrients for bacterial growth during fermentation, the cultures were supplemented with glucose and yeast extracts according to the fermented states of bacteria. When the cultures reached an $OD_{600}$ value of 80-100, an inducer, IPTG, was added to the cultures in an amount of 20 μM to 4 mM to induce protein expression. The cultures were further cultured for 40 to 45 hrs until the OD value at 600 nm increased to 100 to 120.

The expression of immunoglobulin Fc in the *E. coli* transformants and the expressed sites, water solubility and dimer formation of the expressed Ig Fc were examined as follows. To determine whether an expressed product is secreted to the fermentation fluid or the periplasmic space of *E. coli* by the signal sequence fused to the expression vector, the fermentation fluid was centrifuged to obtain a cell-free fermentation fluid and collect cells. The cell-free fermentation fluid and a periplasmic space solution obtained by osmotic shock of the collected cells were subjected to Western blot analysis. As a result, a very small amount of immunoglobulin Fc was detected. To investigate intracellular expression of Ig Fc, cells were disrupted using an ultrasonicator (Misonix Company). The resulting cell lysate was centrifuged to separate water-soluble substances from water-insoluble substances, and the water-soluble substances were subjected to Western blot analysis, as follows. The water-soluble substances were mixed with a protein sample buffer not containing a reducing agent such as DTT or β-mercaptoethanol, and separated on a 15% SDS-PAGE gel (Criterion Gel, Bio-Rad). Then, proteins were transferred onto a nitrocellulose membrane and detected with an HRP-conjugated anti-human Fc antibody (Sigma). As shown in FIG. 1, immunoglobulin Fc was overexpressed in a water-soluble form and located in the cytosol of *E. coli*. Also, products, expressed by transformants transformed with expression vectors expressing Ig Fc having a portion of a hinge region, were expressed as dimers. In FIG. 1, lanes 1, 2 and 3 show products expressed in HM10927, HM10932 and HM10936, respectively, and lane 4 shows Fc generated by papain treatment of immunoglobulins produced in animal cells, which showed a slightly larger size due to its sugar moieties on the SDS-PAGE gel than that produced in *E. coli*.

<4-2> N-terminal Sequence Analysis

The water-soluble dimeric Ig Fc fragments, which were located in the cytosol of *E. coli* as demonstrated in the above <4-1>, were designed to be translated in a fused form to a signal sequence. Thus, to determine whether the Ig Fc fragments are located in *E. coli* cytosol in a form fused to the signal sequence when not secreted without signal sequence processing, N-terminal amino acid sequences of the Ig Fc fragments were determined by the Basic Science Research Institute, Seoul, Korea. Samples used in the N-terminal amino acid sequence analysis were prepared as follows.

First, a PVDF membrane (Bio-Rad) was immersed in methanol for about 2-3 sec to be activated, and was sufficiently wet with a blocking buffer (170 mM glycine, 25 mM Tris-HCl (pH 8.0), 20% methanol). The protein samples separated on a non-reduced SDS-PAGE gel, prepared in the above <4-1>, were blotted onto a PVDF membrane for about one hour using a blotting kit (Hoefer Semi-Dry Transfer unit, Amersham). Proteins transferred onto the PVDF membrane were stained with a protein dye, Coomassie Blue R-250 (Amnesco), for 3-4 sec, and washed with a destaining solution (water:acetic acid:methanol=5:1:4). Then, regions containing proteins from the membrane were cut out with scissors and subjected to N-terminal sequence analysis.

As a result, the IgG1 Fc protein was found to have an N-terminal sequence of Pro-Cys-Pro-Ala-Pro-Glu-Leu-Leu-Gly-Gly, the IgG4 Fc protein had an N-terminal sequence of Ser-Cys-Pro-Ala-Pro-Glu-Phe-Leu-Gly-Gly, and the IgG2 Fc protein had an N-terminal sequence of Pro-Cys-Pro-Ala-Pro-Pro-Val-Ala-Gly-Pro. As apparent from these results, the Fc fragments expressed by the *E. coli* transformants of the present invention were found to have an accurate N-terminal sequence. These results indicate that, when expressed in a form fused to a signal sequence, the Fc fragments are not secreted to the extracellular membrane or periplasmic space, are accurately processed in the signal sequence even upon overexpression and are present in a water-soluble form in the cytosol.

<4-3> Purification of Immunoglobulin Fc

Immunoglobulin Fc was purified using a protein-A affinity column known to have strong affinity to immunoglobulins, as follows.

*E. coli* cells collected by centrifuging fermentation fluids were disrupted by a microfluizer (Microfludics) to give cell lysates. The cell lysates were subjected to two-step column chromatography to purify recombinant immunoglobulin Fc fragments present in the cytosol. 5 ml of a protein-A affinity column (Pharmacia) was equilibrated with PBS, and the cell lysates were loaded onto the column at a flow rate of 5 ml/min. Unbound proteins were washed out with PBS, and bound proteins were eluted with 100 mM citrate (pH 3.0). The collected fractions were desalted using a HiPrep 26/10 desalting column (Pharmacia) with 10 mM Tris buffer (pH 8.0). Then, secondary anion exchange column chromatography was carried out using 50 ml of a Q HP 26/10 column (Pharmacia). The primary purified recombinant immunoglobulin Fc fractions were loaded onto the Q-Sepharose HP 26/10 column, and the column was eluted with a linear gradient of 0-0.2 M NaCl in 10 mM Tris buffer (pH 8.0), thus providing highly pure fractions. After being partially purified using the protein-A affinity column, expression levels of the recombinant Ig Fc fragments were determined as follows.

| Expression vectors | Transformants | Protein expression levels after protein A purification (mg/l) |
|---|---|---|
| pSTIIdCG1Fc | HM10927 | 400 |
| pSTIIG1Mo | HM10930 | 500 |
| pSTIIdCG4Fc | HM10932 | 400 |
| pSTIIG4Mo | HM10933 | 600 |
| pSTIIdCG2Fc | HM10936 | 100 |

Since the immunoglobulin Fc proteins thus obtained are present in a dimeric or monomeric form of the heavy chain, they have different migration patterns on reduced SDS-PAGE and non-reduced SDS-PAGE. The results of SDS-PAGE analysis, performed to determine protein purities after expressed products were purified, are given in FIGS. 2 and 3.

Figure 2:
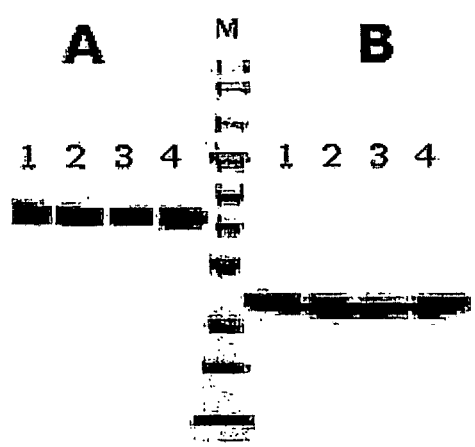
FIGS. 2 and 3 show the results of SDS-PAGE of immunoglobulin Fc fragments under non-reduced and reduced conditions using a 15% criterion gel (Bio-Rad)
Figure 3:
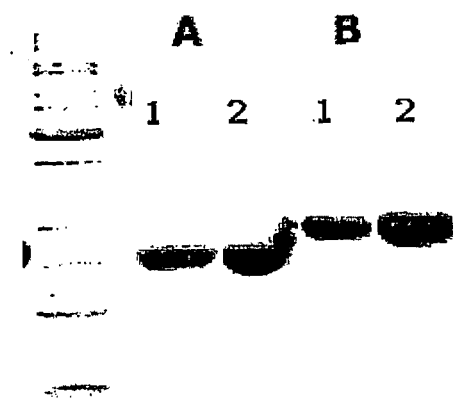

FIGS. 2 and 3 show the results of SDS-PAGE analysis of the purified immunoglobulin Fc fragments in a dimeric or monomeric form under non-reduced and reduced conditions using a criterion gel (Bio-Rad), wherein the Fc fragments were evaluated for differential migration on reduced versus non-reduced gels. In FIG. 2, the A region shows proteins separated on a non-reduced SDS-PAGE gel, and the B region shows proteins on a reduced SDS-PAGE gel. Lane M indicates a prestained low-range standard protein marker (Bio-Rad), and lanes 1 to 4 indicate protein samples for immunoglobulin Fc produced by *E. coli* transformants, HM10927, HM10928 (deposited at the Korean Culture Center of Microorganisms (KCCM) on Sep. 15, 2004 and assigned accession number KCCM-10589), HM10929 (deposited at KCCM on Sep. 15, 2004 and assigned accession number KCCM-10594) and HM10932, respectively. As shown in FIG. 2, on reduced SDS-PAGE, the Ig Fc fragments were present in a monomeric form because disulfide bonds formed between cysteine residues of the hinge region were reduced, and were thus migrated the monomer distance. In contrast, on non-reduced SDS-PAGE, the Ig Fc fragments were present in a dimeric form by disulfide bonds and thus had a migration distance of about 42 kDa.

In FIG. 3, the A region shows proteins separated on a non-reduced SDS-PAGE gel, and the B region shows proteins on a reduced SDS-PAGE gel. Lane M indicates the standard protein marker, and lanes 1 and 2 indicate protein samples for immunoglobulin Fc produced by *E. coli* transformants, HM10930 and HM10933, respectively. As shown in FIG. 3, the proteins did not show a large difference in migration on reduced versus non-reduced gels, and only displayed a slightly different migration due to the reduction of intramolecular disulfide bonds.

Preparation of Conjugate of Immunoglobulin Fc and Drug

Example 5

Preparation I of IFNα-PEG-Immunoglobulin Fc Fragment Conjugate

<Step 1> Preparation of Immunoglobulin Fc Fragment Using Immunoglobulin

Figure 4:
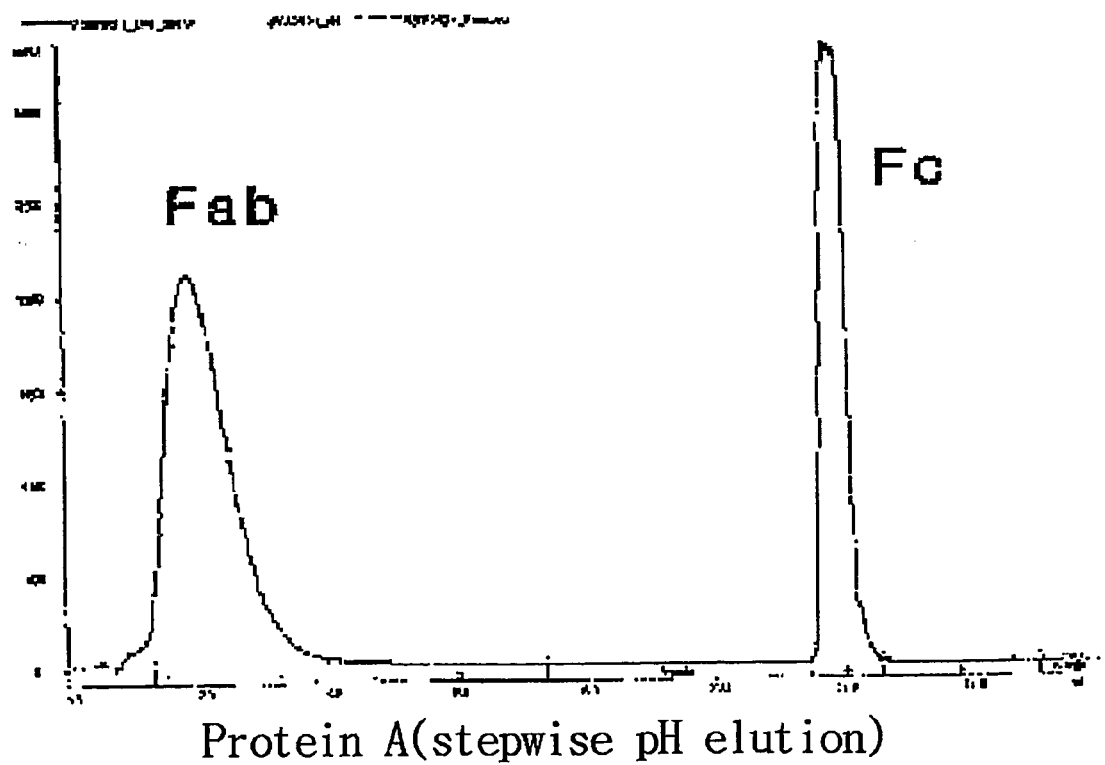
FIG. 4 shows the results of chromatography of an immunoglobulin Fc fragment obtained by cleavage of an immunoglobulin with papain.
Figure 5:
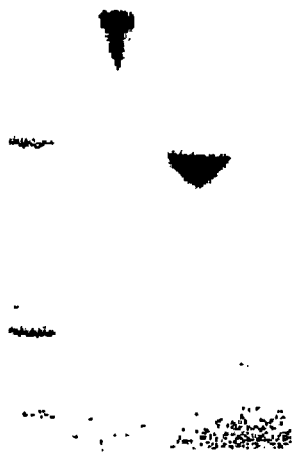
FIG. 5 shows the results of SDS-PAGE of a purified immunoglobulin Fc fragment (M: molecular size marker, lane 1: IgG, lane 2: Fc)

An immunoglobulin Fc fragment was prepared as follows. 200 mg of 150-kDa immunoglobulin G (IgG) (Green Cross, Korea) dissolved in 10 mM phosphate buffer was treated with 2 mg of a proteolytic enzyme, papain (Sigma) at 37° C. for 2 hrs with gentle agitation. After the enzyme reaction, the immunoglobulin Fc fragment regenerated thus was subjected to chromatography for purification using sequentially a Superdex column, a protein A column and a cation exchange column. In detail, the reaction solution was loaded onto a Superdex 200 column (Pharmacia) equilibrated with 10 mM sodium phosphate buffer (PBS, pH 7.3), and the column was eluted with the same buffer at a flow rate of 1 ml/min. Unreacted immunoglobulin molecules (IgG) and F(ab')2, which had a relatively high molecular weight compared to the immunoglobulin Fc fragment, were removed using their property of being eluted earlier than the Ig Fc fragment. Fab fragments having a molecular weight similar to the Ig Fc fragment were eliminated by protein A column chromatography (FIG. 4). The resulting fractions containing the Ig Fc fragment eluted from the Superdex 200 column were loaded at a flow rate of 5 ml/min onto a protein A column (Pharmacia) equilibrated with 20 mM phosphate buffer (pH 7.0), and the column was washed with the same buffer to remove proteins unbound to the column. Then, the protein A column was eluted with 100 mM sodium citrate buffer (pH 3.0) to obtain highly pure immunoglobulin Fc fragment. The Fc fractions collected from the protein A column were finally purified using a cation exchange column (polyCAT, PolyLC Company), wherein this column loaded with the Fc fractions was eluted with a linear gradient of 0.15-0.4 M NaCl in 10 mM acetate buffer (pH 4.5), thus providing highly pure Fc fractions. The highly pure Fc fractions were analyzed by 12% SDS-PAGE (lane 2 in FIG. 5).

<Step 2> Preparation of IFNα-PEG Complex 3.4-kDa polyethylene glycol having an aldehyde reactive group at both ends, ALD-PEG-ALD (Shearwater), was mixed with human interferon alpha-2b (hIFNα-2b, MW: 20 kDa) dissolved in 100 mM phosphate buffer in an amount of 5 mg/ml at an IFNα:PEG molar ratio of 1:1, 1:2.5, 1:5, 1:10 and 1:20. To this mixture, a reducing agent, sodium cyanoborohydride (NaCNBH$_3$, Sigma), was added at a final concentration of 20 mM and was allowed to react at 4° C. for 3 hrs with gentle agitation to allow PEG to link to the amino terminal end of interferon alpha. To obtain a 1:1 complex of PEG and interferon alpha, the reaction mixture was subjected to size exclusion chromatography using a Superdex® column (Pharmacia). The IFNα-PEG complex was eluted from the column using 10 mM potassium phosphate buffer (pH 6.0) as an elution buffer, and interferon alpha not linked to PEG, unreacted PEG and dimer byproducts where PEG was linked to two interferon alpha molecules were removed. The purified IFNα-PEG complex was concentrated to 5 mg/ml. Through this experiment, the optimal reaction molar ratio for IFNα to PEG, providing the highest reactivity and generating the smallest amount of byproducts such as dimers, was found to be 1:2.5 to 1:5.

<Step 3> Preparation of IFNα-PEG-Fc Conjugate

To link the IFNα-PEG complex purified in the above step 2 to the N-terminus of an immunoglobulin Fc fragment, the immunoglobulin Fc fragment (about 53 kDa) prepared in the above step 1 was dissolved in 10 mM phosphate buffer and mixed with the IFNα-PEG complex at an IFNα-PEG complex:Fc molar ratio of 1:1, 1:2, 1:4 and 1:8. After the phosphate buffer concentration of the reaction solution was adjusted to 100 mM, a reducing agent, NaCNBH$_3$, was added to the reaction solution at a final concentration of 20 mM and was allowed to react at 4° C. for 20 hrs with gentle agitation. Through this experiment, the optimal reaction molar ratio for IFNα-PEG complex to Fc, providing the highest reactivity and generating the fewest byproducts such as dimers, was found to be 1:2.

<Step 4> Isolation and Purification of the IFNα-PEG-Fc Conjugate

After the reaction of the above step 3, the reaction mixture was subjected to Superdex size exclusion chromatography so as to eliminate unreacted substances and byproducts and purify the IFNα-PEG-Fc protein conjugate produced. After the reaction mixture was concentrated and loaded onto a Superdex column, 10 mM phosphate buffer (pH 7.3) was passed through the column at a flow rate of 2.5 ml/min to remove unbound Fc and unreacted substances, followed by column elution to collect IFNα-PEG-Fc protein conjugate fractions. Since the collected IFNα-PEG-Fc protein conjugate fractions contained a small amount of impurities, unreacted Fc and interferon alpha dimers, cation exchange chromatography was carried out to remove the impurities. The IFNα-PEG-Fc protein conjugate fractions were loaded onto a PolyCAT LP column (PolyLC) equilibrated with 10 mM sodium acetate (pH 4.5), and the column was eluted with a linear gradient of 0-0.5 M NaCl in 10 mM sodium acetate buffer (pH 4.5) using 1 M NaCl. Finally, the IFNα-PEG-Fc protein conjugate was purified using an anion exchange column. The IFNα-PEG-Fc protein conjugate fractions were loaded onto a PolyWAX LP column (PolyLC) equilibrated with 10 mM Tris-HCl (pH 7.5), and the column was then eluted with a linear gradient of 0-0.3 M NaCl in 10 mM Tris-HCl (pH 7.5) using 1 M NaCl, thus isolating the IFNα-PEG-Fc protein conjugate in a highly pure form.

Example 6

Preparation II of IFNα-PEG-Fc Protein Conjugate

<Step 1> Preparation of Fc-PEG Complex 3.4-kDa polyethylene glycol having an aldehyde reactive group at both ends, ALD-PEG-ALD (Shearwater), was mixed with the immunoglobulin Fc fragment prepared in the step 1 of Example 5 at Fc:PEG molar ratios of 1:1, 1:2.5, 1:5, 1:10 and 1:20, wherein the Ig Fc fragment had been dissolved in 100 mM phosphate buffer in an amount of 15 mg/ml. To this mixture, a reducing agent, NaCNBH₃ (Sigma), was added at a final concentration of 20 mM and was allowed to react at 4° C. for 3 hrs with gentle agitation. To obtain a 1:1 complex of PEG and Fc, the reaction mixture was subjected to size exclusion chromatography using a Superdex® column (Pharmacia). The Fc-PEG complex was eluted from the column using 10 mM potassium phosphate buffer (pH 6.0) as an elution buffer, and immunoglobulin Fc fragment not linked to PEG, unreacted PEG and dimer byproducts where PEG was linked to two immunoglobulin Fc fragment molecules were removed. The purified Fc-PEG complex was concentrated to about 15 mg/ml. Through this experiment, the optimal reaction molar ratio for Fc to PEG, providing the highest reactivity and generating the fewest byproducts such as dimers, was found to be 1:3 to 1:10.

<Step 2> Formation and Purification of Conjugate of the Fc-PEG Complex and Interferon Alpha To link the Fc-PEG complex purified in the above step 1 to the N-terminus of IFNα, the Fc-PEG complex was mixed with IFNα dissolved in 10 mM phosphate buffer at Fc-PEG complex:IFNα molar ratios of 1:1, 1:1.5, 1:3 and 1:6. After the phosphate buffer concentration of the reaction solution was adjusted to 100 mM, a reducing agent, NaCNBH₃, was added to the reaction solution at a final concentration of 20 mM and was allowed to react at 4° C. for 20 hrs with gentle agitation. After the reaction was completed, unreacted substances and byproducts were removed according to the same purification method as in the step 4 of Example 5, thus isolating the Fc-PEG-IFNα protein conjugate in a highly pure form.

Example 7

Preparation of hGH-PEG-Fc Conjugate

An hGH-PEG-Fc conjugate was prepared and purified according to the same method as in Example 5, except that drug other than interferon alpha, human growth hormone (hGH, MW: 22 kDa) was used and a hGH:PEG molar ratio was 1:5.

Example 8

Preparation of (G-CSF)-PEG-Fc Conjugate

A (G-CSF)-PEG-Fc conjugate was prepared and purified according to the same method as in Example 5, except that drug other than interferon alpha, human granulocyte colony stimulating factor (G-CSF), was used and an G-CSF:PEG molar ratio was 1:5.

On the other hand, a ¹⁷S-G-CSF-PEG-Fc protein conjugate was prepared and purified according to the same method as described above using a G-CSF derivative, ¹⁷S-G-CSF, having a serine substitution at the seventeenth amino acid residue of the native G-CSF.

Example 9

Preparation of EPO-PEG-Fc Conjugate

An EPO-PEG-Fc conjugate was prepared and purified according to the same method as in Example 5, except that drug other than interferon alpha, human erythropoietin (EPO), was used and an EPO:PEG molar ratio was 1:5.

Example 10

Preparation of Protein Conjugate Using PEG Having Different Reactive Group

An IFNα-PEG-Fc protein conjugate was prepared using PEG having a succinimidyl propionate (SPA) reactive group at both ends, as follows. 3.4-kDa polyethylene glycol, SPA-PEG-SPA (Shearwater), was mixed with 10 mg of interferon alpha dissolved in 100 mM phosphate buffer at IFNα:PEG molar ratios of 1:1, 1:2.5, 1:5, 1:10 and 1:20. The mixture was then allowed to react at room temperature with gentle agitation for 2 hrs. To obtain a 1:1 complex of PEG and interferon alpha (IFNα-PEG complex), where PEG was linked selectively to the amino group of a lysine residue of interferon alpha, the reaction mixture was subjected to Superdex size exclusion chromatography. The IFNα-PEG complex was eluted from the column using 10 mM potassium phosphate buffer (pH 6.0) as an elution buffer, and interferon alpha not linked to PEG, unreacted PEG and dimer byproducts in which two interferon alpha molecules were linked to both ends of PEG were removed. To link the IFNα-PEG complex to the amino group of a lysine residue of immunoglobulin Fc, the purified IFNα-PEG complex was concentrated to about 5 mg/ml, and an IFNα-PEG-Fc conjugate was prepared and purified according to the same methods as in the steps 3 and 4 of Example 5. Through this experiment, the optimal reaction molar ratio for IFNα to PEG, providing the highest reactivity and generating the fewest byproducts such as dimers, was found to be 1:2.5 to 1:5.

On the other hand, another IFNα-PEG-Fc conjugate was prepared according to the same methods as described above using PEG) having an N-hydroxysuccinimidyl (NHS) reactive group at both ends, NHS-PEG-NHS (Shearwater), or PEG having a buthyl aldehyde reactive group at both ends, BUA-PEG-BUA (Shearwater).

Example 11

Preparation of Protein Conjugate Using PEG Having Different Molecular Weight

An IFNα-10K PEG complex was prepared using 10-kDa polyethylene glycol having an aldehyde reactive group at both ends, ALD-PEG-ALD (Shearwater). This complex was prepared and purified according to the same method as in the step 2 of Example 5. Through this experiment, the optimal reaction molar ratio for IFNα to 10-kDa PEG, providing the highest reactivity and generating the fewest byproducts such as dimers, was found to be 1:2.5 to 1:5. The purified IFNα-10K PEG complex was concentrated to about 5 mg/ml, and, using this concentrate, an IFNα-10K PEG-Fc conjugate was prepared and purified according to the same methods as in the steps 3 and 4 of Example 5.

Example 12

Preparation of Fab'-S-PEG-N-Fc Conjugate (-SH Group)

<Step 1> Expression and Purification of Fab'

An *E. coli* transformant, BL21/poDLHF (accession number: KCCM-10511), expressing anti-tumor necrosis factor-alpha Fab', was grown in 100 ml of LB medium overnight with agitation, and was inoculated in a 5-L fermentor (Marubishi) and cultured at 30° C. and 500 rpm and at an air flow rate of 20 vvm. To compensate for the insufficient nutrients for bacterial growth during fermentation, the cultures were supplemented with glucose and yeast extracts according to the fermented states of bacteria. When the cultures reached an $OD_{600}$ value of 80-100, an inducer, IPTG, was added to the cultures to induce protein expression. The cultures were further cultured for 40 to 45 hrs until the OD value at 600 nm increased to 120 to 140. The fermentation fluid thus obtained was centrifuged at 20,000×g for 30 min. The supernatant was collected, and the pellet was discarded.

The supernatant was subjected to the following three-step column chromatography to purify anti-tumor necrosis factor-alpha Fab'. The supernatant was loaded onto a HiTrap protein G column (5 ml, Pharmacia) equilibrated with 20 mM phosphate buffer (pH 7.0), and the column was eluted with 100 mM glycine (pH 3.0). The collected Fab' fractions were then loaded onto a Superdex 200 column (Pharmacia) equilibrated with 10 mM sodium phosphate buffer (PBS, pH 7.3), and this column was eluted with the same buffer. Finally, the second Fab' fractions were loaded onto a polyCAT 21×250 column (PolyLC), and this column was eluted with a linear NaCl gradient of 0.15-0.4 M in 10 mM acetate buffer (pH 4.5), thus providing highly pure anti-tumor necrosis factor-alpha Fab' fractions.

<Step 2> Preparation and Purification of Fc-PEG Complex

To link a PEG linker to the N-terminus of an immunoglobulin Fc, the immunoglobulin Fc prepared according to the same method as in the step 1 of Example 5 was dissolved in 100 mM phosphate buffer (pH 6.0) at a concentration of 5 mg/ml, and was mixed with NHS-PEG-MAL (3.4 kDa, Shearwater) at an Fc:PEG molar ratio of 1:10, followed by incubation at 4° C. for 12 hrs with gentle agitation.

After the reaction was completed, the reaction buffer was exchanged with 20 mM sodium phosphate buffer (pH 6.0) to remove unbound NHS-PEG-MAL. Then, the reaction mixture was loaded onto a polyCAT column (PolyLC). The column was eluted with a linear NaCl gradient of 0.15-0.5 M in 20 mM sodium phosphate buffer (pH 6.0). During this elution, the immunoglobulin Fc-PEG complex was eluted earlier than unreacted immunoglobulin Fc, and the unreacted Ig Fc was eluted later, thereby eliminating the unreacted Ig Fc molecules.

<Step 3> Preparation and Purification of Fab'-S-PEG-N-Fc Conjugate (-SH Group)

To link the immunoglobulin Fc-PEG complex to a cysteine group of the Fab', the Fab' purified in the above step 1 was dissolved in 100 mM sodium phosphate buffer (pH 7.3) at a concentration of 2 mg/ml, and was mixed with the immunoglobulin Fc-PEG complex prepared in the above step 2 at a Fab':complex molar ratio of 1:5. The reaction mixture was concentrated to a final protein concentration of 50 mg/ml and incubated at 4° C. for 24 hrs with gentle agitation.

After the reaction was completed, the reaction mixture was loaded onto a Superdex 200 column (Pharmacia) equilibrated with 10 mM sodium phosphate buffer (pH 7.3), and the column was eluted with the same buffer at a flow rate of 1 ml/min. The coupled Fab'-S-PEG-N-Fc conjugate was eluted relatively earlier due to its high molecular weight, and unreacted immunoglobulin Fc-PEG complex and Fab' were eluted later, thereby eliminating the unreacted molecules. To completely eliminate unreacted immunoglobulin Fc-PEG, the collected Fab'-S-PEG-N-Fc conjugate fractions were again loaded onto a polyCAT 21×250 column (PolyLC), and this column was eluted with a linear NaCl gradient of 0.15-0.5 M in 20 mM sodium phosphate buffer (pH 6.0), thus providing a pure Fab'-S-PEG-N-Fc conjugate comprising the Fc-PEG complex linked to an -SH group near the C-terminus of the Fab'.

Example 13

Preparation of Fab'-N-PEG-N-Fc Conjugate (N-Terminus)

<Step 1> Preparation and Purification of Fab'-PEG Complex (N-terminus)

40 mg of the Fab' purified in the step 1 of Example 12 was dissolved in 100 mM sodium phosphate buffer (pH 6.0) at a concentration of 5 mg/ml, and was mixed with butyl ALD-PEG-butyl ALD (3.4 kDa, Nektar) at a Fab':PEG molar ratio of 1:5. A reducing agent, $NaCNBH_3$, was added to the reaction mixture at a final concentration of 20 mM, and the reaction mixture was then allowed to react at 4° C. for 2 hrs with gentle agitation.

After the reaction was completed, the reaction buffer was exchanged with 20 mM sodium phosphate buffer (pH 6.0). Then, the reaction mixture was loaded onto a polyCAT column (PolyLC). The column was eluted with a linear NaCl gradient of 0.15-0.4 M in 20 mM acetate buffer (pH 4.5). During this column elution, the Fab'-PEG complex comprising the PEG linker lined to the N-terminus of the Fab' was eluted earlier than unreacted. Fab', and the unreacted Fab' was eluted later, thereby eliminating the unreacted Fab' molecules.

<Step 2> Preparation and Purification of Fab'-N-PEG-N-Fc Conjugate

To link the Fab'-PEG complex purified in the above step 1 to the N-terminus of an immunoglobulin Fc, the Fab'-PEG complex was dissolved in 100 mM sodium phosphate buffer (pH 6.0) at a concentration of 10 mg/ml, and was mixed with the immunoglobulin Fc dissolved in the same buffer at a Fab'-PEG complex:Fc molar ratio of 1:5. After the reaction mixture was concentrated to a final protein concentration of 50 mg/ml, a reducing agent, NaCNBH$_3$, was added to the reaction mixture at a final concentration of 20 mM, and the reaction mixture was then reacted at 4° C. for 24 hrs with gentle agitation.

After the reaction was completed, the reaction mixture was loaded onto a Superdex 200 column (Pharmacia) equilibrated with 10 mM sodium phosphate buffer (pH 7.3), and the column was eluted with the same buffer at a flow rate of 1 ml/min. The coupled Fab'-N-PEG-N-Fc conjugate was eluted relatively earlier due to its high molecular weight, and unreacted immunoglobulin Fc and Fab'-PEG complex were eluted later, thereby eliminating the unreacted molecules. To completely eliminate the unreacted immunoglobulin Fc molecules, the collected Fab'-N-PEG-N-Fc conjugate fractions were again loaded onto a polyCAT 21×250 column (PolyLC), and this column was eluted with a linear NaCl gradient of 0.15-0.5 M in 20 mM sodium phosphate buffer (pH 6.0), thus providing a pure Fab'-N-PEG-N-Fc conjugate comprising the immunoglobulin Fc-PEG complex linked to the N-terminus of the Fab'.

Example 14

Preparation and Purification of Deglycosylated Immunoglobulin Fc 200 mg of an immunoglobulin Fc prepared according to the same method as in Example 5 was dissolved in 100 mM phosphate buffer (pH 7.5) at a concentration of 2 mg/ml, and was mixed with 300 U/mg of a deglycosylase, PNGase F (NEB). The reaction mixture was allowed to react at 37° C. for 24 hrs with gentle agitation. Then, to purify the deglycosylated immunoglobulin Fc, the reaction mixture was loaded onto a SP Sepharose FF column (Pharmacia), and the column was eluted with a linear NaCl gradient of 0.1-0.6 M in 10 mM acetate buffer (pH 4.5) using 1 M NaCl. The native immunoglobulin Fc was eluted earlier, and the deglycosylated immunoglobulin Fc (DG Fc) was eluted later.

Example 15

Preparation of IFNα-PEG-DG Fc Conjugate

To link the deglycosylated immunoglobulin Fc prepared in Example 14 to the IFNα-PEG complex purified in the step 2 of Example 5, the IFNα-PEG complex was mixed with the DG Fc dissolved in 10 mM phosphate buffer at IFNα-PEG complex: DG Fc molar ratios of 1:1, 1:2, 1:4 and 1:8. After the phosphate buffer concentration of the reaction solution was adjusted to 100 mM, a reducing agent, NaCNBH$_3$, was added to the reaction solution at a final concentration of 20 mM and was allowed to react at 4° C. for 20 hrs with gentle agitation. Through this experiment, the optimal reaction molar ratio for IFNα-PEG complex to DG Fc, providing the highest reactivity and generating the fewest byproducts such as dimers, was found to be 1:2.

After the coupling reaction, the reaction mixture was subjected to size exclusion chromatography using a SuperdexR column (Pharmacia) so as to eliminate unreacted substances and byproducts and purify the IFNα-PEG-DG Fc protein conjugate. After the reaction mixture was loaded onto the column, a phosphate buffer (pH 7.3) was passed through the column at a flow rate of 2.5 ml/min to remove unbound DG Fc and unreacted substances, followed by column elution to collect IFNα-PEG-DG Fc protein conjugate fractions. Since the collected IFNα-PEG-DG Fc protein conjugate fractions contained a small amount of impurities, unreacted DG Fc and IFNα-PEG complex, cation exchange chromatography was carried out to remove the impurities. The IFNα-PEG-DG Fc protein conjugate fractions were loaded onto a PolyCAT LP column (PolyLC) equilibrated with 10 mM sodium acetate (pH 4.5), and the column was eluted with a linear gradient of 0-0.6 M NaCl in 10 mM sodium acetate buffer (pH 4.5) using 1 M NaCl. Finally, the IFNα-PEG-DG Fc protein conjugate was purified using an anion exchange column. The IFNα-PEG-Fc protein conjugate fractions were loaded onto a Poly-WAX LP column (PolyLC) equilibrated with 10 mM Tris-HCl (pH 7.5), and the column was then eluted with a linear gradient of 0-0.3 M NaCl in 10 mM Tris-HCl (pH 7.5) using 1 M NaCl, thus isolating the IFNα-PEG-DG Fc protein conjugate in a highly pure form.

Example 16

Preparation of Conjugate of IFNα-PEG Complex and Recombinant AG Fc Derivative

According to the same methods as in Examples 5 and 15, the IFNα-PEG complex was linked to the N terminus of the IgG4 delta-Cys as an AG Fc derivative prepared in Example 1. After the coupling reaction, unreacted substances and byproducts were removed from the reaction mixture, and the thus-produced IFNα-PEG-AG Fc protein conjugate (I) was primarily purified using 50 ml of a Q HP 26/10 column (Pharmacia) and further purified by a high-pressure liquid chromatographic assay using a polyCAT 21.5×250 column (polyLC), thus purifying the conjugate to a high degree. The coupling reaction solution was desalted using a HiPrep 26/10 desalting column (Pharmacia) with 10 mM Tris buffer (pH 8.0). Then, the reaction solution was then loaded onto 50 ml of a Q HP 26/10 column (Pharmacia) at a flow rate of 8 ml/min, and this column was eluted with a linear NaCl gradient of 0-0.2 M to obtain desired fractions. The collected fractions were again loaded onto a polyCAT 21.5×250 column equilibrated with 10 mM acetate buffer (pH 5.2) at a flow rate of 15 ml/min, and this column was eluted with a linear NaCl gradient of 0.1-0.3 M, thus providing highly pure fractions. According to the same method as described above, another IFNα-PEG-AG Fc protein conjugate (II) was prepared using another AG Fc derivative prepared in Example 12, IgG4 monomer.

Example 17

Preparation of EPO-PEG-Recombinant AG Fc Derivative Conjugate

According to the same method as in Example 16, an EPO-PEG-recombinant AG Fc derivative conjugate was prepared by linking an AG Fc derivative, IgG4 delta-Cys, to the EPO-PEG complex.

Comparative Example 1

Preparation of IFNα-40K PEG Complex 5 mg of interferon alpha was dissolved in 100 mM phosphate buffer to obtain a final volume of 5 ml, and was mixed with 40-kDa activated methoxy-PEG-aldehyde (Shearwater), at an IFNα:40-kDa PEG molar ratio of 1:4. To this mixture, a reducing agent, NaCNBH$_3$ was added at a final concentration of 20 mM and was allowed to react at 4° C. for 18 hrs with gentle agitation. To inactivate PEG, which did not react with IFNα, Ethanolamine was added to the reaction mixture at a final concentration of 50 mM.

A Sephadex G-25 column (Pharmacia) was used to remove unreacted PEG and exchange the buffer with another buffer. First, this column was equilibrated with two column volumes (CV) of 10 mM Tris-HCl buffer (pH 7.5), and was loaded with the reaction mixture. Flow throughs were detected by measuring the absorbance at 260 nm using a UV spectrophotometer. When the column was eluted with the same buffer, interferon alpha modified by adding PEG having a higher molecular weight to its N-terminus was eluted earlier, and unreacted PEG was eluted later, thus allowing isolation of only IFNα-40K PEG.

The following chromatography was carried out to further purify the IFNα-40K PEG complex from the collected fractions. 3 ml of a PolyWAX LP column (PolyLC) was equilibrated with 10 mM Tris-HCl (pH 7.5). The collected fractions containing the IFNα-40K PEG complex was loaded onto the column at a flow rate of 1 ml/min, and the column was washed with 15 ml of the equilibrium buffer. Then, the column was eluted with a linear NaCl gradient of 0-100% using 30 ml of 1 M NaCl, thus eluting interferon alpha conjugated to tri-, di- and mono-PEG, sequentially. To further purify the mono-PEG-conjugated interferon alpha, the collected fractions containing the mono-PEG-conjugated interferon alpha were subjected to size exclusion chromatography. The fractions were concentrated and loaded onto a Superdex 200 column (Pharmacia) equilibrated with 10 mM sodium phosphate buffer (pH 7.0), and the column was eluted with the same buffer at a flow rate of 1 ml/min. The tri- and di-PEG-conjugated interferon alpha molecules were removed based on their property of being eluted earlier than the mono-PEG-conjugated interferon alpha, thus isolating the mono-PEG-conjugated interferon alpha in a highly pure form.

According to the same method as described above, 40-kDa PEG was conjugated to the N-terminus of human growth hormone, granulocyte colony stimulating factor (G-CSF), and a derivative of G-CSF, thus providing hGH-40K PEG, G-CSF-40K PEG and 40K PEG-[17]S-G-CSF derivative complexes.

Comparative Example 2

Preparation of IFNα-PEG-albumin Conjugate

To link the IFNα-PEG complex purified in the step 2 of Example 1 to the N-terminus of albumin, the IFNα-PEG complex was mixed with human serum albumin (HSA, about 67 kDa, Green Cross) dissolved in 10 mM phosphate buffer at an IFNα-PEG complex:albumin molar ratio of 1:1, 1:2, 1:4 and 1:8. After the phosphate buffer concentration of the reaction solution was adjusted to 100 mM, a reducing agent, NaCNBH$_3$, was added to the reaction solution at a final concentration of 20 mM and was allowed to react at 4° C. for 20 hrs with gentle agitation. Through this experiment, the optimal reaction molar ratio for IFNα-PEG complex to albumin, providing the highest reactivity and generating the fewest byproducts such as dimers, was found to be 1:2.

After the coupling reaction, the reaction mixture was subjected to size exclusion chromatography using a Superdex® column (Pharmacia) so as to eliminate unreacted substances and byproducts and purify the IFNα-PEG-albumin protein conjugate produced. After the reaction mixture was concentrated and loaded onto the column, 10 mM sodium acetate buffer passed through the column at a flow rate of 2.5 ml/min to remove unbound albumin and unreacted substances, followed by column elution to purify only IFNα-PEG-albumin protein conjugate. Since the collected IFNα-PEG-albumin protein conjugate fractions contained a small amount of impurities, unreacted albumin and interferon alpha dimers, cation exchange chromatography was carried out to remove the impurities. The IFNα-PEG-albumin protein conjugate fractions were loaded onto a SP5PW column (Waters) equilibrated with 10 mM sodium acetate (pH 4.5), and the column was eluted with a linear gradient of 0-0.5 M NaCl in 10 mM sodium acetate buffer (pH 4.5) using 1 M NaCl, thus isolating the IFNα-PEG-albumin protein conjugate in a highly pure form.

According to the same method as described above, albumin was conjugated to human growth hormone, G-CSF, and a derivative of G-CSF, thus providing hGH-PEG-albumin, G-CSF-PEG-albumin and [17]S-G-CSF-PEG-albumin conjugates.

Comparative Example 3

Preparation of Fab'-S-40K PEG Complex

The free cysteine residue of the Fab' purified in the step 1 of Example 8 was activated by incubation in an activation buffer (20 mM sodium acetate (pH 4.0), 0.2 mM DTT) for 1 hr. After the buffer was exchanged by a PEG modification buffer, 50 mM potassium phosphate (pH 6.5), maleimide-PEG (MW: 40 kDa, Shearwater) was added thereto at a Fab':40-kDa PEG molar ratio of 1:10 and was reacted to react at 4° C. for 24 hrs with gentle agitation.

After the reaction was completed, the reaction solution was loaded onto a Superdex 200 column (Pharmacia) equilibrated with 10 mM sodium phosphate buffer (pH 7.3), and the column was eluted with the same buffer at a flow rate of 1 ml/min. The Fab' conjugated 40-kDa PEG (Fab'-40K PEG) was eluted relatively earlier due to its high molecular weight, and unreacted Fab' was eluted later, thereby eliminating the unreacted Fab'. To completely eliminate the unreacted Fab', the collected Fab'-40K PEG complex fractions were again loaded onto a polyCAT 21×250 column (PolyLC), and this column was eluted with a linear NaCl gradient of 0.15-0.5 M in 20 mM sodium phosphate buffer (pH 4.5), thus providing a pure Fab'-S-40K PEG complex comprising 40-kDa PEG linked to an -SH group of the Fab'.

Experimental Example 1

Identification and Quantitative Analysis of the Protein Conjugates

<1-1> Identification of the Protein Conjugates

Figure 6:
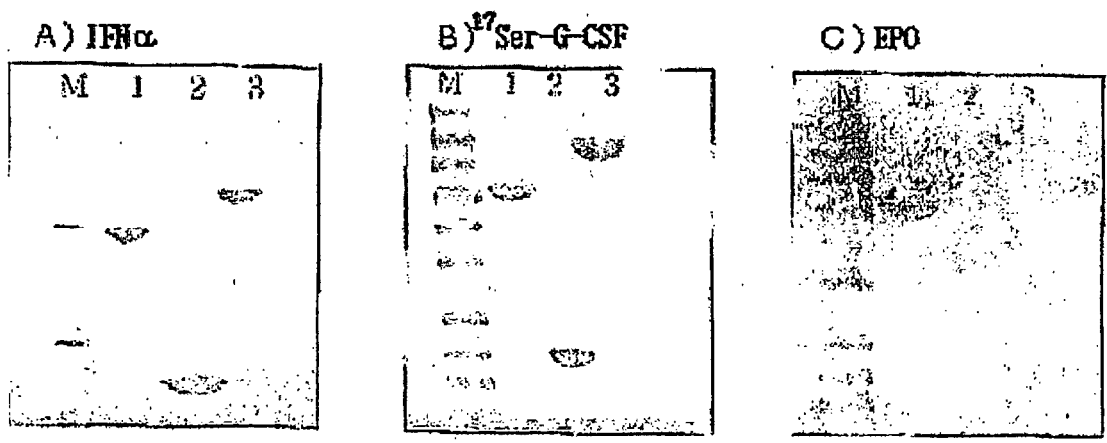
FIG. 6 shows the results of SDS-PAGE of IFNα-PEG-Fc (A), $^{17}$Ser-G-CSF-PEG-Fc (B) and EPO-PEG-Fc (C) conjugates, which are generated by a coupling reaction (M: molecular size marker, lane 1: Fc, lane 2: physiologically active protein, lane 3: physiologically active protein-PEG-Fc conjugate)

The protein conjugates prepared in the above Examples were analyzed by non-reduced SDS-PAGE using a 4-20% gradient gel and a 12% gel and ELISA (R&D System). As a result of SDS-PAGE analysis, as shown in FIG. 6, a coupling reaction of a physiological polypeptide, a non-peptide polymer, PEG, and an immunoglobulin Fc fragment resulted in the successful production of an IFNα-PEG-Fc conjugate (A), a [17]Ser-G-CSF-PEG-Fc conjugate (B) and an EPO-PEG-Fc conjugate (C).

In addition, the DG Fc prepared in Example 10 was analyzed by non-reduced 12% SDS-PAGE. As shown in FIG. 9*b*, a DG Fc band was detected at a position, which corresponds to the molecular weight of the native Fc lacking sugar moieties.

<1-2> Quantitative Analysis of the Protein Conjugates

Figure 7:
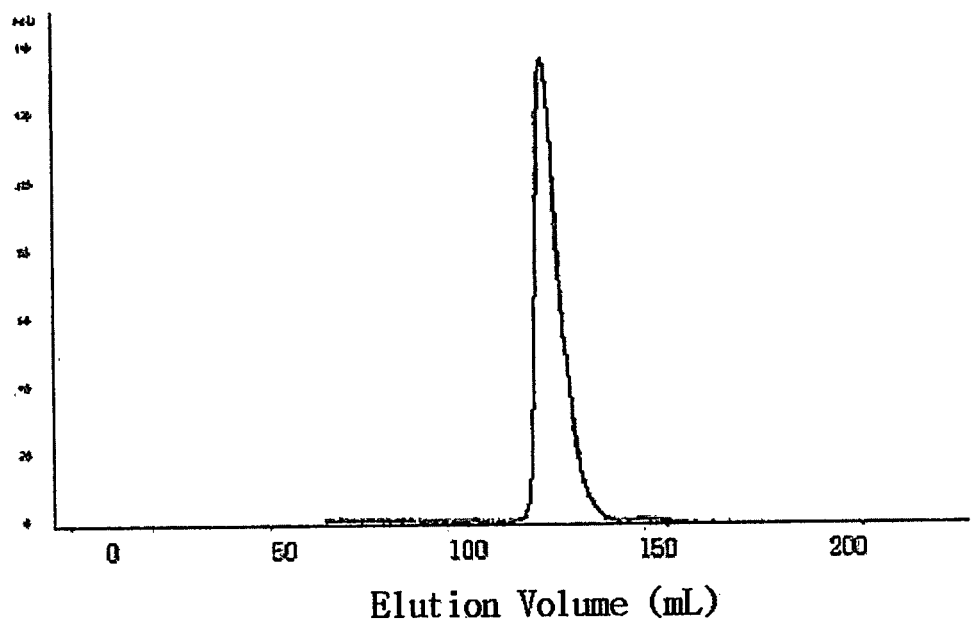
FIG. 7 shows the results of size exclusion chromatography of an IFNα-PEG-Fc conjugate that is purified after a coupling reaction.

The protein conjugates prepared in the above Examples were quantified by size exclusion chromatography using a HiLoad 26/60 Superdex 75 column (Pharmacia) and 10 mM potassium phosphate buffer (pH 6.0) as an elution buffer, wherein a peak area of each protein conjugate was compared to that of a control group. Previously quantitatively analyzed standards, IFNα, hGH, G-CSF, $^{17}$S-G-CSF, EPO and Fc, were individually subjected to size exclusion chromatography, and a conversion factor between a concentration and a peak was determined. A predetermined amount of each protein conjugate was subjected to the same size exclusion chromatography. By subtracting a peak area corresponding to an immunoglobulin Fc fragment from the thus-obtained peak area, a quantitative value for a physiologically active protein present in each protein conjugate was determined. FIG. 7 shows the result of size exclusion chromatography of the purified IFNα-PEG-Fc conjugate, wherein a single peak was observed. This result indicates that the purified protein conjugate does not contain multimeric impurities such as a dimer, a trimer or a higher number of monomers.

When a physiologically active polypeptide conjugated to Fc was quantitatively analyzed using an antibody specific to the physiologically active polypeptide, the antibody was prevented from binding to the polypeptide, resulting in a value lower than an actual value calculated by the chromatography. In the case of the IFNα-PEG-Fc conjugate, an ELISA resulted in an ELISA value corresponding to about 30% of an actual value.

<1-3> Evaluation of Purity and Mass of the Protein Conjugates

The protein conjugates prepared in the above Examples were subjected to size exclusion chromatography, and absorbance was measured at 280 nm. As a result, the IFNα-PEG-Fc, hGH-PEG-Fc, G-CSF-PEG-Fc and $^{17}$Ser-G-CSF-PEG-Fc conjugates displayed a single peak at the retention time of a 70 to 80-kDa substance.

Figure 11A:
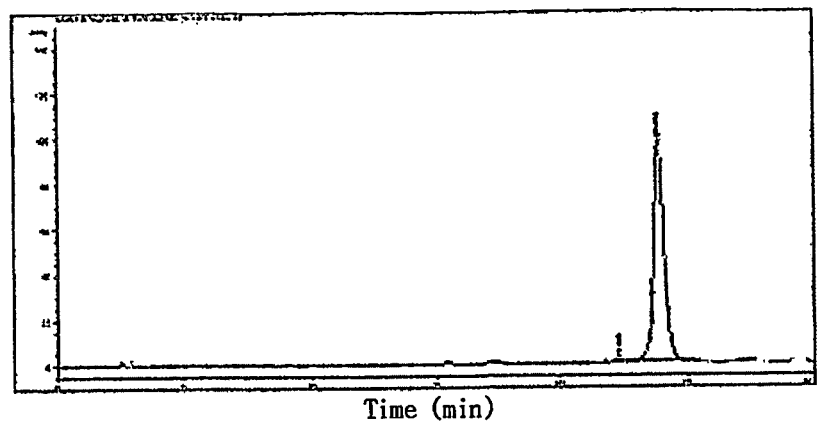
FIGS. 11a to 11c show the results of reverse phase HPLC of IFNα-PEG-Fc, IFNα-PEG-DG Fc and IFNα-PEG-recombinant AG Fc derivative conjugates.
Figure 11B:
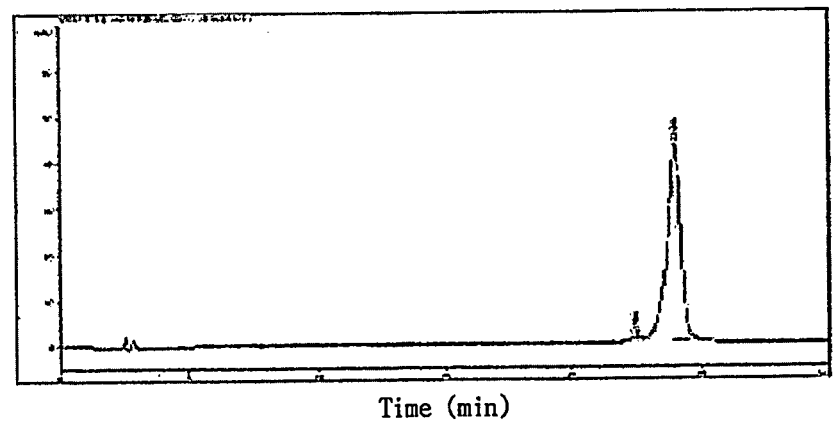
Figure 11C:
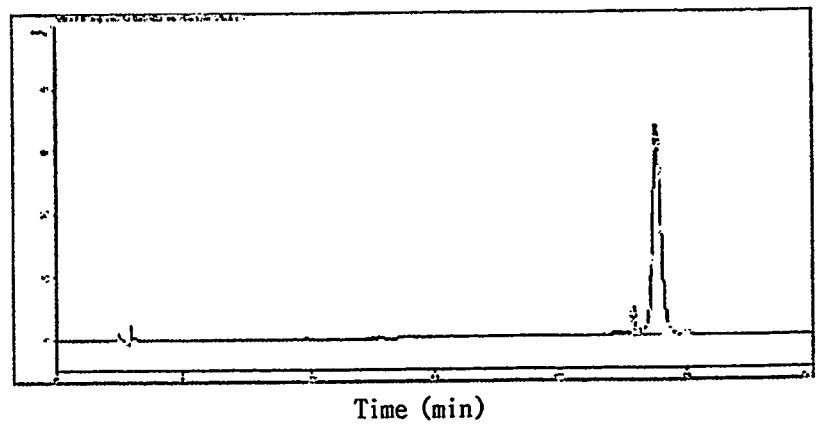

On the other hand, reverse phase HPLC was carried out to determine purities of the protein conjugates prepared in Examples 5, 15 and 16, IFNα-PEG-Fc, IFNα-PEG-DG Fc and IFNα-PEG-recombinant AG Fc derivative. A reverse phase column (259 VHP54 column, Vydac) was used. The column was eluted with a 40-100% acetonitrile gradient with 0.5% TFA, and purities were analyzed by measuring absorbance at 280 nm. As a result, as shown in FIG. 11, the samples contain no unbound interferon or immunoglobulin Fc, and all of the protein conjugates, IFNα-PEG-Fc (A), IFNα-PEG-DG Fc (B) and IFNα-PEG-recombinant AG Fc derivative (C), were found to have a purity greater than 96%.

To determine accurate molecular weights of the purified protein conjugates, mass for each conjugate was analyzed using a high-throughput MALDI-TOF mass spectrophotometer (Voyager DE-STR, Applied Biosystems). Sinapinic acid was used as a matrix. 0.5 μl of each test sample was coated onto a sample slide and air-dried, again mixed with the equal volume of a matrix solution and air-dried, and introduced into an ion source. Detection was carried out in a positive fashion using a linear mode TOF analyzer. Ions were accelerated with a split extraction source operated with delayed extraction (DE) using a delayed extraction time of 750 nsec to 1500 nsec at a total acceleration voltage of about 2.5 kV.

Figure 8:
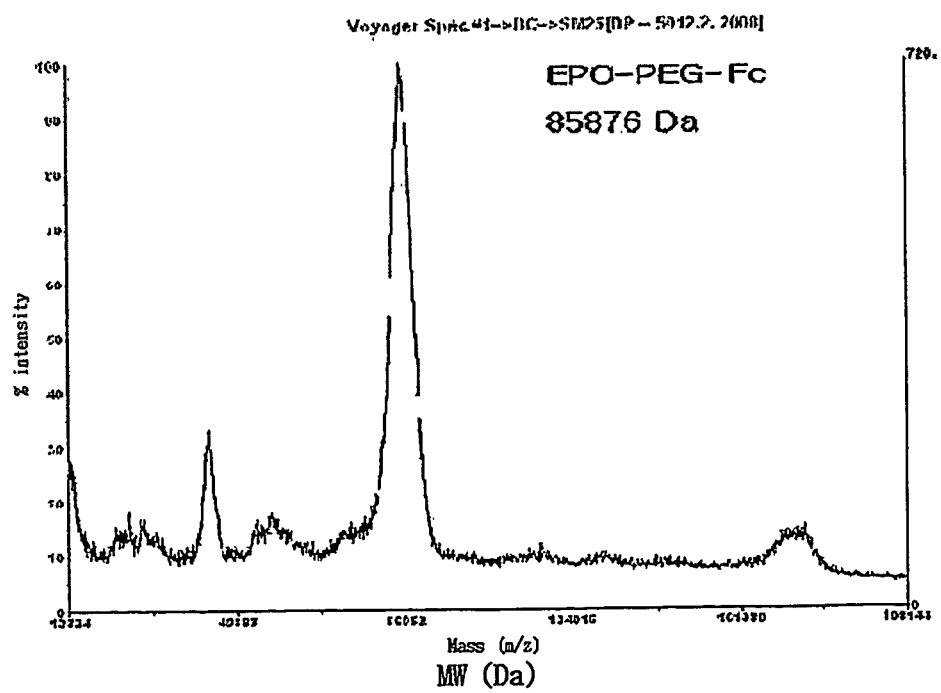
FIG. 8 shows the results of MALDI-TOF mass spectrometry of an EPO-PEG-Fc conjugate.
Figure 10:
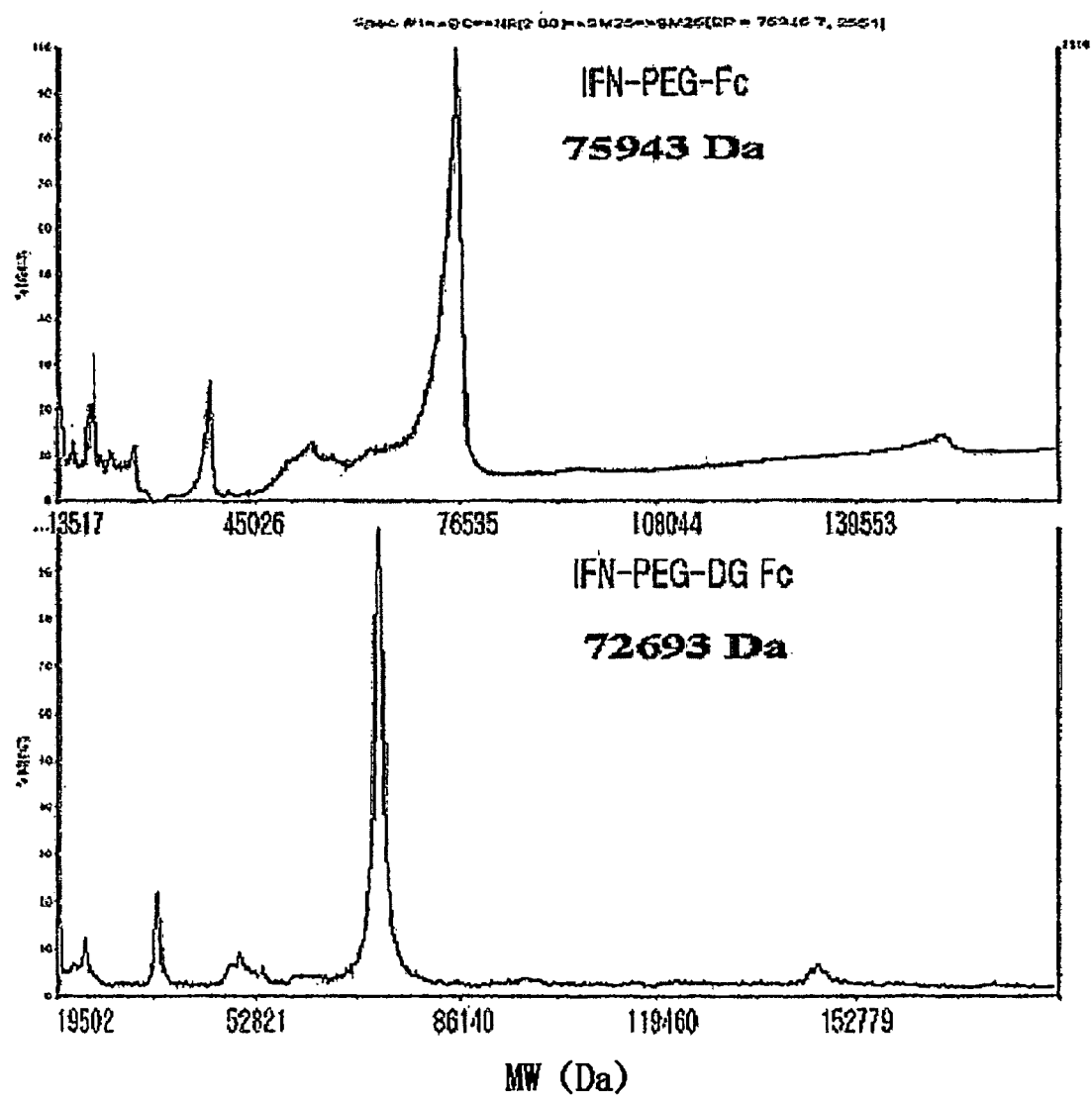
FIG. 10 shows the results of MALDI-TOF mass spectrometry of an IFNα-PEG-Fc conjugate and an IFNα-PEG-DG Fc conjugate.

The molecular weights observed by MALDI-TOF mass spectrometry for the Fc protein conjugates prepared in Examples are given in Table 1, below. FIG. 8 shows the result of MALDI-TOF mass spectrometry of the EPO-PEG-Fc conjugate, and FIG. 10 shows the results of MALDI-TOF mass spectrometry of the IFNα-PEG-Fc and IFNα-PEG-DG Fc conjugates. As a result, the EPO-PEG-Fc protein conjugate was found to have a purity of more than 95% and a molecular weight very close to a theoretical MW. Also, EPO was found to couple to the immunoglobulin Fc fragment at a ratio of 1:1.

TABLE 1

|  | Theoretical MW (kDa) | Measured MW (kDa) |
|---|---|---|
| IFNα-PEG-Fc (E. 1) | 75.4 | 75.9 |
| hGH-PEG-Fc (E. 3) | 78.4 | 78.6 |
| G-CSF-PEG-Fc (E. 4) | 75.3 | 75.9 |
| $^{17}$S-G-CSF derivative-PEG-Fc (E. 4) | 75.0 | 75.9 |
| EPO-PEG-Fc (E. 5) | 91.4 | 91.0 |

Figure 9A:
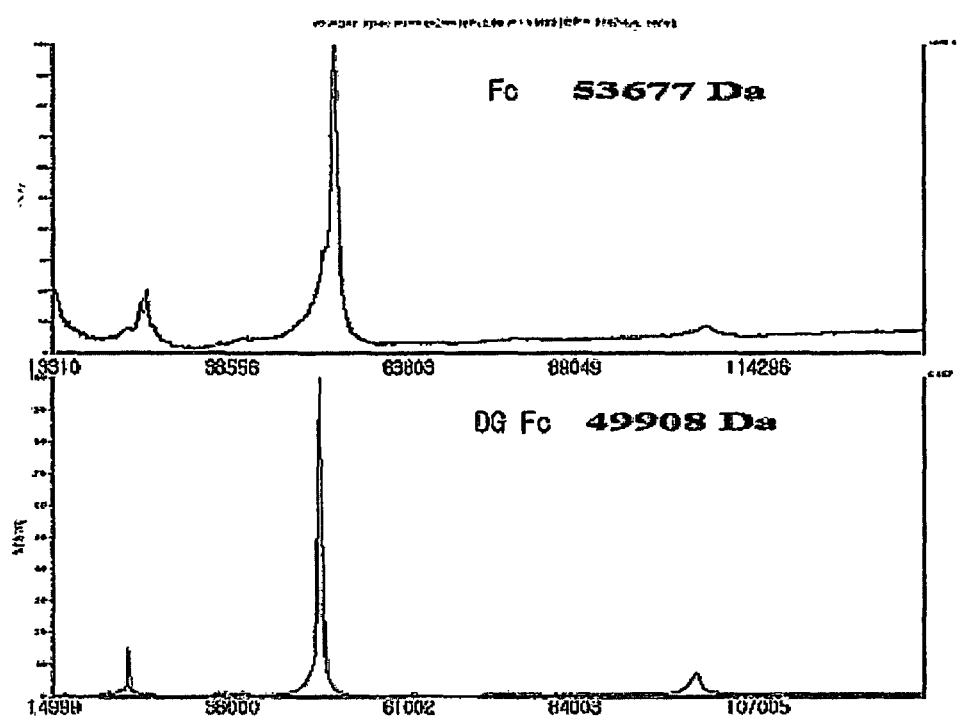
FIGS. 9a and 9b show the results of MALDI-TOF mass spectrometry and SDS-PAGE analysis, respectively, of a native immunoglobulin Fc and a deglycosylated immunoglobulin Fc (DG Fc)
Figure 9B:
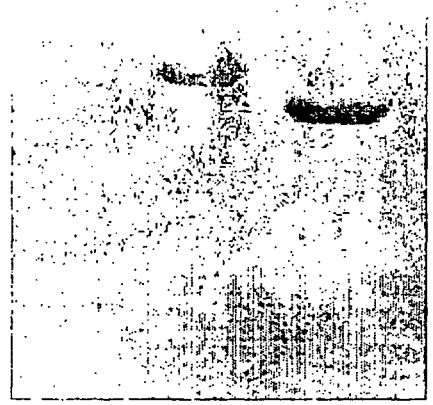

In addition, when the Fc and DG Fc prepared in Example 14 were examined for their molecular weights by MALDI-TOF mass spectrometry, the DG Fc was found to be 50 kDa, which is about 3-kDa less than native Fc (FIG. 9a). Since the 3-kDa MW corresponds to the theoretical size of sugar moieties, the results demonstrate that the sugar moieties are completely removed.

Table 2, below, shows the results of MALDI-TOF mass spectrometry of the IFNα-PEG-DG Fc conjugate prepared in Example 11 and the IFNα-PEG-recombinant AG Fc derivative conjugates (I and II) prepared in Example 16. The IFNα-PEG-DG Fc conjugate was found to be 3 kDa lighter, and the IFNα-PEG-recombinant AG Fc derivative conjugate (I) to be about 3-4 kDa lighter, than the IFNα-PEG-Fc conjugate of 75.9 kDa. The IFNα-PEG-recombinant AG Fc derivative conjugate (II) coupled to an Fc monomer showed a molecular weight decreased by 24.5 kDa corresponding to the molecular weight of the Fc monomer.

TABLE 2

|  | Theoretical MW (kDa) | Measured MW (kDa) |
|---|---|---|
| IFNα-PEG-DG Fc (E. 11) | 72.8 | 73.0 |
| IFNα-PEG-recombinant AG Fc derivative (I) (E. 13) | 72.3 | 72.2 |
| IFNα-PEG-recombinant AG Fc derivative (II) (E. 13) | 46.8 | 46.6 |

Experimental Example 2

Pharmacokinetic Analysis I

Native forms of physiologically active proteins (controls) and the protein complexes prepared in Examples and Comparative Examples, -40K PEG complexes, -PEG-albumin conjugates, -PEG-Fc conjugates, -PEG-DG Fc conjugates and -PEG-recombinant AG Fc derivative conjugates, were evaluated for serum stability and pharmacokinetic parameters in SD rats (five rats per group). The controls, and the -40K PEG complexes, -PEG-albumin conjugates, -PEG-Fc conjugates, -PEG-DG Fc conjugates and -PEG-recombinant AG Fc derivative conjugates (test groups) were individually injected subcutaneously at a dose of 100 μg/kg. After the subcutaneous injection, blood samples were collected at 0.5, 1, 2, 4, 6, 12, 24, 30, 48, 72 and 96 hrs in the control groups, and, in the test groups, at 1, 6, 12, 24, 30, 48, 72, 96, 120, 240 and 288 hrs. The blood samples were collected in tubes with an anticoagulant, heparin, and centrifuged for 5 min using an Eppendorf high-speed micro centrifugator to remove blood cells. Serum protein levels were measured by ELISA using antibodies specific to the physiologically active proteins.

The results of pharmacokinetic analyses of the native forms of IFNα, hGH, G-CSF and EPO, and -40K PEG complexes thereof, -PEG-albumin conjugates thereof, -PEG-Fc conjugates thereof and -PEG-DG Fc conjugates thereof, are given in Tables 3 to 7, below. In the following tables, $T_{max}$ indicates the time taken to reach the maximal drug serum concentration, $T_{1/2}$ indicates the serum half-life of a drug, and MRT (mean residence time) indicates the mean time that a drug molecule resides in the body.

TABLE 3

Pharmacokinetics of interferon alpha

| | Native IFNα | IFNα-40K PEG (C.E. 1) | IFNα-PEG-albumin (C.E. 2) | IFNα-PEG-Fc (E. 5) | IFNα-PEG-DG Fc (E. 15) | IFNα-PEG-recombinant AG Fc derivative (I) (E. 16) | IFNα-PEG-recombinant AG Fc derivative (II) (E. 16) |
|---|---|---|---|---|---|---|---|
| $T_{max}$ (hr) | 1.0 | 30 | 12 | 30 | 48 | 24 | 24 |
| $T_{1/2}$ (hr) | 1.7 | 35.8 | 17.1 | 90.4 | 71.0 | 61.2 | 31.2 |
| MRT (hr) | 2.1 | 71.5 | 32.5 | 150.1 | 120.6 | 111.0 | 58.8 |

TABLE 4

Pharmacokinetics of human growth factor

| | Native hGH | hGH-40K PEG (C.E. 1) | hGH-PEG-albumin (C.E. 2) | hGH-PEG-Fc (E. 7) |
|---|---|---|---|---|
| $T_{max}$ (hr) | 1.0 | 12 | 12 | 12 |
| $T_{1/2}$ (hr) | 1.1 | 7.7 | 5.9 | 11.8 |
| MRT (hr) | 2.1 | 18.2 | 13.0 | 18.8 |

TABLE 5

Pharmacokinetics of G-CSF

| | Native G-CSF | G-CSF-40K PEG (C.E. 1) | G-CSF-PEG-albumin (C.E. 2) | G-CSF-PEG-Fc (E. 8) |
|---|---|---|---|---|
| $T_{max}$ (hr) | 2.0 | 12 | 12 | 12 |
| $T_{1/2}$ (hr) | 2.8 | 4.8 | 5.2 | 6.9 |
| MRT (hr) | 5.2 | 24.5 | 25.0 | 32.6 |

TABLE 6

Pharmacokinetics of $^{17}$S-G-CSF derivative

| | Native $^{17}$S-G-CSF derivative | $^{17}$S-G-CSF-40K PEG (C.E. 1) | $^{17}$S-G-CSF-PEG-albumin (C.E. 2) | $^{17}$S-G-CSF-PEG-Fc (E. 8) |
|---|---|---|---|---|
| $T_{max}$ (hr) | 2.0 | 24 | 24 | 24 |
| $T_{1/2}$ (hr) | 2.9 | 4.3 | 6.4 | 7.0 |
| MRT (hr) | 5.8 | 24.4 | 25.1 | 33.2 |

TABLE 7

Pharmacokinetics of EPO

| | Native EPO | Highly glycosylated EPO | EPO-PEG-Fc (E. 9) | EPO-PEG-recombinant AG Fc derivative (E. 17) |
|---|---|---|---|---|
| $T_{max}$ (hr) | 6.0 | 12 | 30 | 48 |
| $T_{1/2}$ (hr) | 9.4 | 18.4 | 61.5 | 87.9 |
| MRT (hr) | 21.7 | 26.8 | 117.6 | 141.6 |

Figure 12:
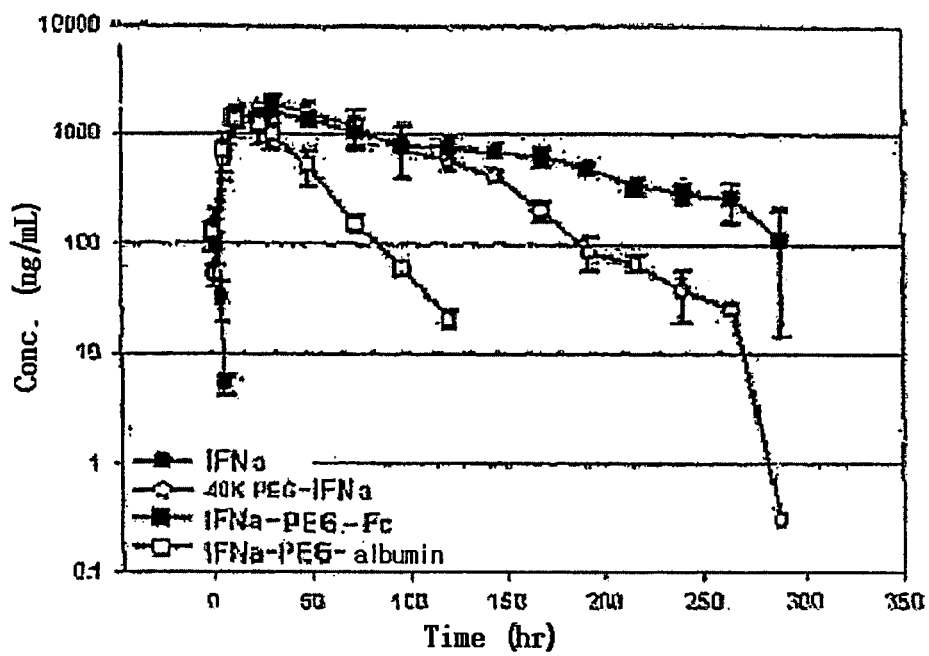
FIG. 12 is a graph showing the results of pharmacokinetic analysis of a native IFNα, an IFNα-40K PEG complex, an IFNα-PEG-albumin conjugate and an IFNα-PEG-Fc conjugate.

As shown from the data of Table 13 and the pharmacokinetic graph of FIG. 12, the IFNα-PEG-Fc protein conjugate had a serum half-life of 90.4 hrs, which was about 50 times higher than that of native IFNα and about 2.5 times higher than that of IFNα-40K PEG having a half-life of 35.8 hrs, prepared in Comparative Example 1. Also, the IFNα-PEG-Fc protein conjugate of the present invention was found to be superior in serum half-life to IFNα-PEG-albumin, which has a half-life of 17.1 hrs.

Figure 14:
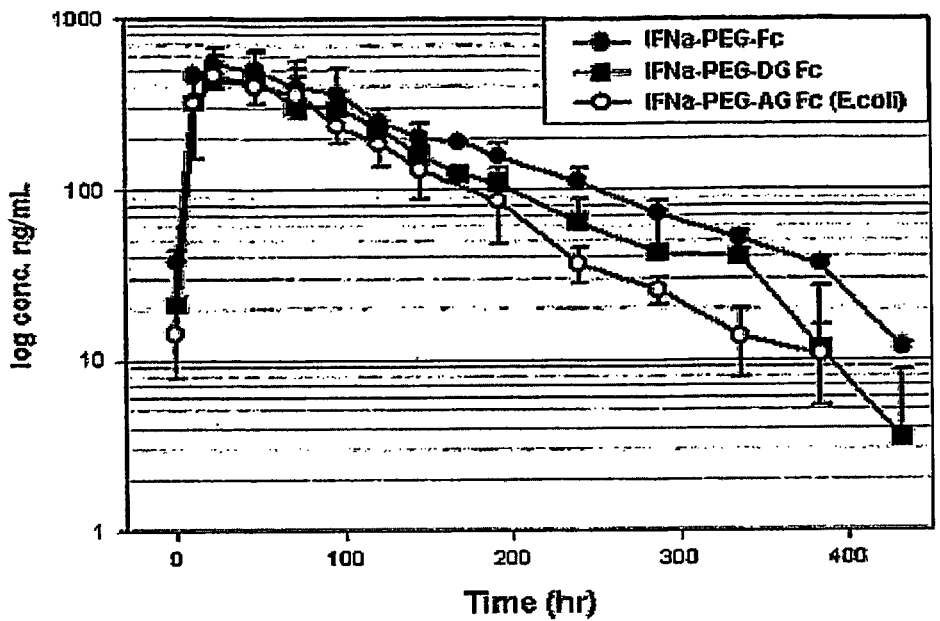
FIG. 14 is a graph showing the results of pharmacokinetic analysis of IFNα-PEG-Fc, IFNα-PEG-DG Fc and IFNα-PEG-recombinant AG Fc conjugates.

On the other hand, as shown in Table 3 and FIG. 14, the IFNα-PEG-DG Fc conjugate had a serum half-life of 71.0 hrs, which was almost the same as the IFNα-PEG-Fc conjugate, indicating that the deglycosylation of Fc does not greatly affect the in vivo stability of the IFNα-PEG-DG Fc conjugate. Also, the conjugate prepared using the recombinant AG Fc derivative produced by a recombinant method was found to have an effect identical to that of the native form-derived DG Fc. However, the serum half-life of a complex coupled to an Fc monomer was about half that of a complex coupled to a normal Fc dimer.

As shown in Table 4, human growth hormone also showed an extended serum half-life when conjugated to the IgG Fc fragment according to the present invention. That is, compared to the native form (1.1 hrs), the hGH-40K PEG complex and hGH-PEG-albumin conjugate had slightly increased half-lives of 7.7 hrs and 5.9 hrs, respectively, whereas the hGH-PEG-Fc protein conjugate of the present invention displayed a greatly extended serum half-life of 11.8 hrs.

As apparent from the pharmacokinetic data of G-CSF and its derivative in Table 5 and 6, the G-CSF-PEG-Fc and $^{17}$S-G-CSF-PEG-Fc conjugates displayed a much longer serum half-life than the -40K PEG complex and -PEG-albumin conjugate. The immunoglobulin Fc fragment was found in the serum to prolong the duration of action of physiologically active proteins in native forms, as well as in their derivatives having alterations of certain amino acid residues in similar levels to the native forms. From these results, it is easily predictable that the method of the present invention will have a similar effect on other proteins and their derivatives.

Figure 13:
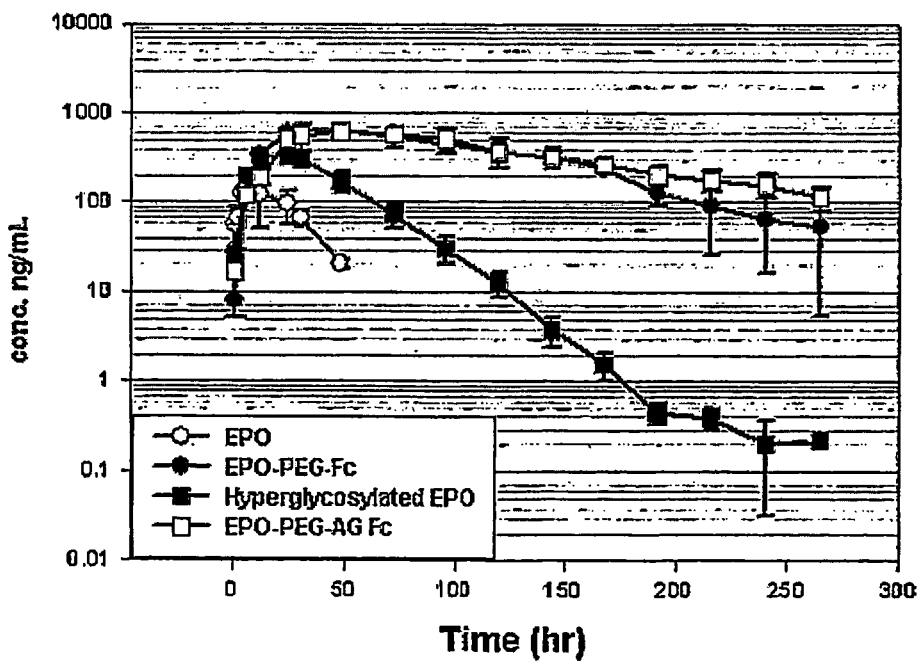
FIG. 13 is a graph showing the results of pharmacokinetic analysis of a native EPO, a highly glycosylated EPO, an EPO-PEG-Fc conjugate and an EPO-PEG-AG Fc conjugate.

As shown in Table 7 and FIG. 13, the conjugation of the native glycosylated EPO to the Fc fragment also resulted in an increase in serum half-life. That is, EPO had a serum half-life of 9.4 hrs in the native form, and a prolonged serum half-life of 18.4 hrs in the Darbepoetin α(Aranesp, Amgen), which is highly glycosylated to improve serum stability. The EPO-PEG-Fc conjugate, comprising EPO coupled to the immunoglobulin Fc fragment according to the present invention, displayed a markedly prolonged serum half-life of 61.5 hrs. Also, when conjugated to the E. coli-derived recombinant aglycosylated (AG) Fc derivative, the half-life of EPO increased to 87.9 hrs, indicating that the aglycosylation of the Fc fragment allows the preparation of a protein conjugate not affecting serum stability of the protein without antibody functions.

As apparent from the above results, the protein conjugates covalent-bonded to the immunoglobulin Fc fragment through a non-peptide polymer according to the present invention displayed serum half-lives increased several to several tens to that of the native form. Also, when the immunoglobulin Fc was aglycosylated by production in E. coli or deglydosylated by enzyme treatment, its effect of increasing the serum half-life of its protein conjugate was maintained at a similar level.

In particular, compared to proteins modified with 40-kDa PEG having the longest duration of action among PEG molecules for increasing the duration of action of proteins in the serum, the immunoglobulin Fc protein conjugates had much superior serum stability. In addition, compared to protein conjugates coupled to albumin instead of the immunoglobulin Fc, the protein conjugates of the present invention displayed excellent serum stability, indicating that the protein conjugates of the present invention are effective in developing long-acting forms of protein drugs. These results, that the present protein conjugates have excellent effects on serum stability and MRT in a broad range of proteins including colony stimulating factor derivatives by point mutation compared to conventional PEG- or albumin-conjugated proteins, indicate that the stability and duration-extending effects of the present protein conjugates are applicable to other physiologically active polypeptides.

On the other hand, when the IFNα-10K PEG-Fc protein conjugate (Example 11) prepared using a non-peptide polymer, 10-kDa PEG, was evaluated for its serum half-life according to the same method as described above, it showed a serum half-life of 48.8 hrs, which was somewhat shorter than the serum half-life (79.7 hrs) of a protein conjugate prepared using 3.4-kDa PEG.

In addition, the serum half-lives of the protein conjugates decreases with increasing molecular weight of the non-peptide polymer PEG. These results indicate that the major factor increasing the serum stability and duration of the protein conjugates is the conjugated immunoglobulin Fc fragment rather than the non-peptide polymer.

Even when the reactive group of PEG was exchanged with a reactive group other than the aldehyde group, protein conjugates with the PEG showed similar patterns in apparent molecular weight and serum half-life to those coupled to PEG having an aldehyde reactive group.

Experimental Example 3

Pharmacokinetic Analysis II

To determine the serum half-lives of the Fab'-S-PEG-N-Fc and Fab'-N-PEG-N-Fc conjugates prepared in Example 12 and 13 and the Fab'-S-40K PEG complex prepared in Comparative Example 3, drug pharmacokinetic analysis was carried out according to the same method as in Experimental Example 2 using Fab' as a control, the conjugates and the complex. The results are given in FIG. 15.

Figure 15:
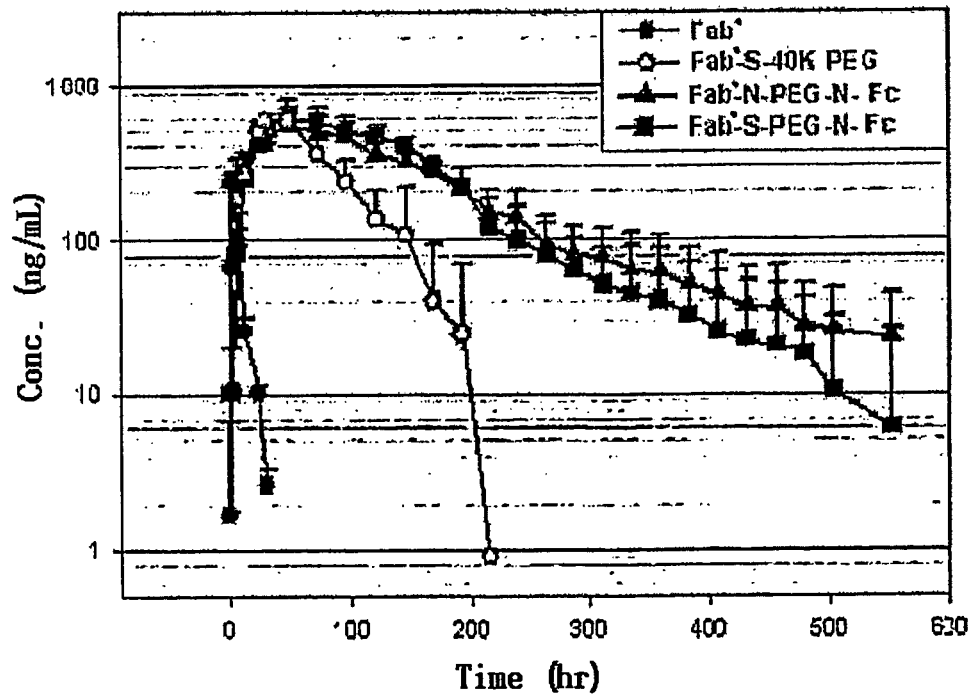
FIG. 15 is a graph showing the pharmacokinetics of a Fab', a Fab'-S-40K PEG complex, a Fab'-N-PEG-N-Fc conjugate and a Fab'-S-PEG-N-Fc conjugate.

As shown in FIG. 15, the Fab'-S-PEG-N-Fc and Fab'-N-PEG-N-Fc conjugates displayed a serum half-life prolonged two or three times compared to the Fab' or Fab'-S-40K PEG complex.

Experimental Example 4

Evaluation of Intracellular Activity of the Protein Conjugates

<4-1> Comparison of the IFNα Protein Conjugates for Intracellular Activity

To compare the intracellular activity of the IFNα protein conjugates, the IFNα-PEG-Fc (Example 5), IFNα-PEG-DG Fc (Example 15), IFNα-PEG-recombinant AG Fc derivative (Example 16), IFNα-40K PEG (Comparative Example 1) and IFNα-PEG-albumin (Comparative Example 2) were evaluated for antiviral activity by a cell culture bioassay using Madin Darby Bovine Kidney (MDBK) cells (ATCC CCL-22) infected with vesicular stomatitis virus. Nonpegylated interferon alpha-2b, available from the National Institute for Biological Standards and Controls (NIBSC), was used as a standard material.

MDBK cells were cultured in MEM (minimum essential medium, JBI) supplemented with 10% FBS and 1% penicillin/streptomycin at 37° C. under 5% $CO_2$ condition. Samples to be analyzed and the standard material were diluted with the culture medium to predetermined concentrations, and 100-μl aliquots were placed onto each well of a 96-well plate. The cultured cells were detached, added to the plate containing the samples in a volume of 100 μl, and cultured for about 1 hr at 37° C. under 5% $CO_2$ condition. Then, 50 μl of vesicular stomatitis virus (VSV) of $5-7\times10^3$ PFU was added to each well of the plate, and the cells were further cultured for about 16 to 20 hrs at 37° C. under 5% $CO_2$ conditions. A well that did not contain the sample or standard material but contained only the virus was used as a negative control, and a well that contained only cells was used as a positive control.

After the culture medium was removed, 100 μl of a neutral red solution was added to the plate to stain viable cells, followed by incubation for 2 hrs at 37° C. under 5% $CO_2$ condition. After the supernatants were removed, 100 μl of a 1:1 mixture of 100% ethanol and 1% acetic acid was added to each well of the plate. After thorough mixing to dissolve all neutral red crystals eluted from stained cells, absorbance was measured at 540 nm. The negative control was used as a blank, and $ED_{50}$ values (doses causing 50% cell growth inhibition) were calculated, where the cell growth of the positive control was set at 100%.

TABLE 8

| | Conc. (ng/ml) | Specific activity (IU/mg) | Relative activity (%) for native IFNα |
|---|---|---|---|
| Native IFNα | 100 | 4.24E+08 | 100 |
| IFNα-40K PEG | 100 | 2.04E+07 | 4.8 |
| IFNα-PEG-albumin | 100 | 2.21E+07 | 5.2 |
| IFNα-PEG-Fc | 100 | 1.19E+08 | 28.1 |
| IFNα-PEG-DG Fc | 100 | 1.09E+08 | 25.7 |
| IFNα-PEG-recombinant AG Fc derivative | 100 | 9.58E+07 | 22.6 |

As shown in Table 8, the IFNα-40K PEG decreased in activity to 4.8% of the native IFNα. Especially, as the size of the PEG moieties increased, a protein conjugate has improved serum stability but gradually decreased activity. Interferon alpha was reported to have in vitro activities of 25% when modified with 12-kDa PEG and about 7% when modified with 40-kDa PEG (P. Bailon et al., *Bioconjugate Chem.* 12: 195-202, 2001). That is, since a protein conjugate has a longer half-life but sharply decreases in biological activity as the molecular weight of PEG moieties increase, there is a need for the development of a protein conjugate having a longer serum half-life and a stronger activity. In addition, the IFNα-PEG-albumin conjugate displayed a weak activity of about 5.2% compared to the native IFNα. In contrast, the IFNα-PEG-Fc and IFNα-PEG-DG Fc conjugates of the present invention exhibited a markedly improved relative activity of 28.1% and 25.7% compared to the native IFNα. Also, the conjugation of IFNα to the recombinant AG Fc derivative resulted in a similar increase in activity. From these results, it is expected that interferon alpha conjugated to the immunoglobulin Fc fragment has a markedly increased serum half-life and greatly improved pharmaceutical efficacy in vivo.

<4-2> Comparison of the Human Growth Hormone Protein Conjugates for Intracellular Activity To compare the intracellular activity of the human growth hormone protein conjugates, the hGH-PEG-Fc, hGH-40K PEG and hGH-PEG-albumin were compared for intracellular activity.

Intracellular activities of the hGH conjugates were measured by an in vitro assay using a rat node lymphoma cell line, Nb2 (European Collection of Cell Cultures (ECACC) #97041101), which develops human growth hormone-dependent mitogenesis.

Nb2 cells were cultured in Fisher's medium supplemented with 10% FBS (fetal bovine serum), 0.075% $NaCO_3$, 0.05 mM 2-mercaptoethanol and 2 mM glutamin, and were further cultured in a similar medium not containing 10% FBS for 24 hrs. Then, the cultured cells were counted, and about $2 \times 10^4$ cells were aliquotted onto each well of a 96-well plate. The hGH-PEG-Fc, the hGH-40K PEG, the hGH-PEG-albumin, a standard available from the National Institute for Biological Standards and Controls (NIBSC) as a control, and native human growth hormone (HM-hGH) were diluted and added to each well at various concentrations, followed by incubation for 48 hrs at 37° C. under 5% $CO_2$ condition. Thereafter, to measure cell proliferation activity by determining the cell number in each well, 25 μl of the Cell Titer 96 Aqueous One Solution Reagent (Promega) was added to each well, and the cells were further cultured for 4 hrs. Absorbance was measured at 490 nm, and a titer for each sample was calculated. The results are given in Table 9, below.

TABLE 9

|  | Conc. (ng/ml) | Specific activity* (U/mg) | Relative activity (%) for native HM-hGH |
| --- | --- | --- | --- |
| Native hGH | 100 | 2.71E+06 | 100 |
| hGH (standard available from NIBSC) | 100 | 2.58E+06 | 95.2 |
| hGH-40K PEG | 100 | 0.206E+06 | 7.6 |
| hGH-PEG-albumin | 100 | 0.141E+06 | 5.2 |
| hGH-PEG-Fc | 100 | 0.76E+06 | 28.1 |

Specific activity* = $1/ED_{50} \times 10^6$ ($ED_{50}$: protein amount required for 50% of maximum cell growth As shown in Table 9, also in the case of human growth hormone, the conjugation to 40-kDa PEG (hGH-40K PEG) resulted in a decrease in activity to about 7.6% of the native form, and the hGH-PEG-albumin conjugate displayed a low in vitro activity that was about 5.2% of the native hGH. However, the hGH-PEG-Fc conjugate of the present invention markedly increased in relative activity to greater than 28% compared to the native hGH. From these results, it is expected that human growth hormone linked to the immunoglobulin Fc fragment has a markedly increased serum half-life and a greatly improved in vivo pharmaceutical efficacy. In addition, it is believed that the increased activity of the immunoglobulin Fc protein conjugates of the present invention is due to the increased serum stability and preserved binding affinity to receptors due to the immunoglobulin Fc or due to the space formed by the non-peptide polymer. These effects are predicted to be applicable to immunoglobulin Fc protein conjugates coupled to other physiologically active proteins.

<4-3> Comparison of the G-CSF Protein Conjugates for Intracellular Activity

To compare the intracellular activity of the protein conjugates with a G-CSF derivative, the native G-CSF (Filgrastim, Jeil Pharm. Co., Ltd.), $^{17}$Ser-G-CSF derivative, 20K PEG-G-CSF (Neulasta), 40K PEG-$^{17}$S-G-CSF, $^{17}$Ser-G-CSF-PEG-albumin and $^{17}$S-G-CSF-PEG-Fc were compared for intracellular activity.

First, a human myeloid cell line, HL-60 (ATCC CCL-240, promyelocytic leukemia patient/36 yr old Caucasian female), was cultured in RPMI 1640 medium supplemented with 10% FBS. The cultured cells were suspended at a density of about $2.2 \times 10^5$ cells/ml, and DMSO (dimethylsulfoxide, culture grade, Sigma) was added thereto at a final concentration of 1.25% (v/v). Then, 90 μl of the cell suspension was seeded onto each well of a 96-well plate (Corning/low evaporation 96 well plate), thus providing a density of about $2 \times 10^4$ cells per well, and cultured in an incubator at 37° C. with 5% $CO_2$ for about 72 hrs.

Each sample, whose protein concentration was determined using a G-CSF ELISA kit (R&D systems), was diluted with RPMI 1640 to an identical concentration of 10 μg/ml, and further diluted two-fold with RPMI 1640 nineteen times. The serial two-fold dilutions were individually added to each well containing HL-60 cells at a volume of 10 μl, so that the concentration of each sample started at 1 μg/ml. Then, the cells were cultured in an incubator at 37° C. for 72 hrs.

The proliferation of HL-60 cells was assayed using Cell Titer 96™ (Cat. NO. G4100, Promega), and the increased cell number was determined by measuring absorbance at 670 nm.

TABLE 10

|  | $ED_{50}$ (IU/mg) | Relative activity (%) for native G-CSF |
| --- | --- | --- |
| Native G-CSF | 0.30 | 100 |
| $^{17}$Ser-G-CSF | 0.26 | 115 |
| G-CSF-20K PEG (Neulasta) | 1.20 | 25 |
| $^{17}$Ser-G-CSF-40K PEG | 10.0 | <10.0 |
| $^{17}$Ser-G-CSF-PEG-albumin | 1.30 | 23.0 |
| $^{17}$Ser-G-CSF-PEG-Fc | 0.58 | 51.7 |

As shown in Table 10, the immunoglobulin Fc protein conjugates coupled to a G-CSF derivative having an amino acid substitution, $^{17}$Ser-G-CSF, also displayed similar effects to native G-CSF-coupled protein conjugates. The $^{17}$Ser-G-CSF-PEG was previously reported to have a relatively increased serum half-life but a decreased activity compared to nonpegylated $^{17}$Ser-G-CSF (Korean Pat. Laid-open Publication No. 2004-83268). Especially, as the size of the PEG moieties increased, a protein conjugate had increased serum stability but gradually decreased activity. The [17]Ser-G-CSF-40K PEG showed a very low activity of less than about 10% compared to the native form. That is, since a protein conjugate has an extended serum half-life but a sharply decreased activity as the molecular weight of PEG moieties increases, there is the need for the development of a protein conjugate having a long serum half-life and strong activity. The [17]Ser-G-CSF-PEG-albumin also showed a low activity of about 23% compared to the native G-CSF. In contrast, the [17]Ser-G-CSF-PEG-Fc was greatly improved in relative activity to more than 51% compared to the native G-CSF. From these results, it is expected that [17]Ser-G-CSF linked to the immunoglobulin Fc fragment has a markedly increased serum half-life and a greatly improved pharmaceutical in vivo efficacy.

<4-4> Cytotoxicity Neutralization Assay for the Fab' Conjugates

An in vitro activity assay was carried out using the Fab'-S-PEG-N-Fc and Fab'-N-PEG-N-Fc conjugates prepared in Example 8 and 9 and the Fab'-S-40K PEG complex prepared in Comparative Example 3. Through a cytotoxicity assay based on measuring TNFα-mediated cytotoxicity, the Fab' conjugates were evaluated to determine whether they neutralize TNFα-induced apoptosis in a mouse fibroblast cell line, L929 (ATCC CRL-2148).

The Fab'-S-PEG-N-Fc and Fab'-N-PEG-N-Fc conjugate and the Fab'-S-40K PEG complex were serially two-fold diluted, and 100-μl aliquots were placed onto wells of a 96-well plate. rhTNF-α (R&D systems) and actinomycin D (Sigma) used as an RNA synthesis inhibitor were added to each well at final concentrations of 10 ng/ml and 1 μg/ml, respectively, incubated for 30 min in an incubator at 37° C. with 5% $CO_2$, and transferred to a microplate for assay. L929 cells were added to each well at a density of $5 \times 10^4$ cells/50 μl medium and cultured for 24 hrs in an incubator at 37° C. with 5% $CO_2$. After the culture medium was removed, 50 μl of MTT (Sigma) dissolved in PBS at a concentration of 5 mg/ml was added to each well, and the cells were further cultured for about 4 hrs in an incubator at 37° C. with 5% $CO_2$. 150 μl of DMSO was added to each well, and the degree of cytotoxicity neutralization was determined by measuring the absorbance at 540 nm. As a control, the Fab' purified in the step 1 of Example 8 was used.

Figure 16:
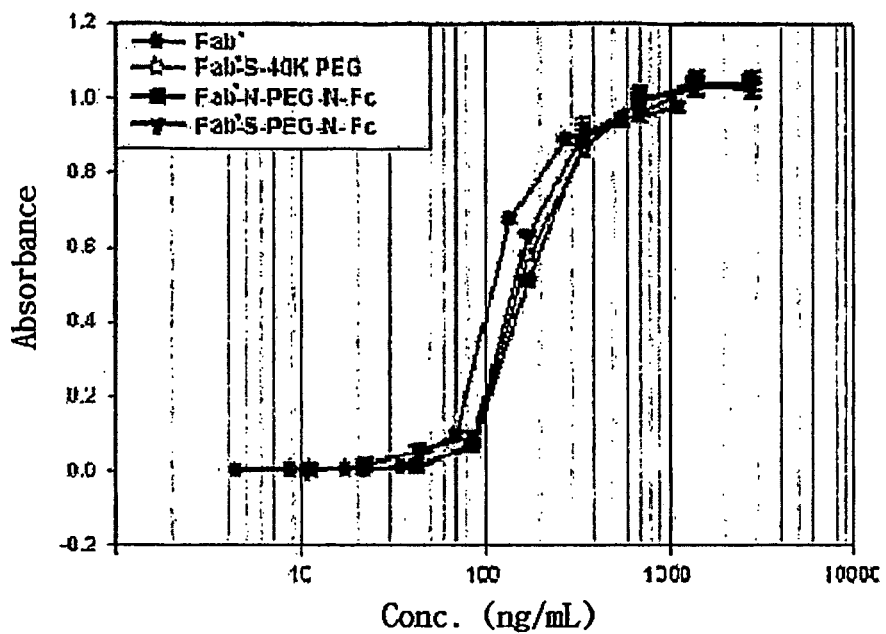
FIG. 16 is a graph showing the in vivo activities of Fab', a Fab'-S-40K PEG complex, a Fab'-N-PEG-N-Fc conjugate and a Fab'-S-PEG-N-Fc conjugate.

As shown in FIG. 16, all of the protein conjugates used in this test had a similar titer to the Fab'. These results indicate that, when a protein conjugate is prepared by linking an immunoglobulin Fc to a free cysteine residue near the N-terminus or C-terminus of a Fab' through PEG, the Fab' exhibits a markedly increased serum half-life and a high in vivo activity.

<4-5> Complement-Dependent Cytotoxicity (CDC) Assay

To determine whether the derivatives prepared in Examples and proteins corresponding to the constant regions of immunoglobulins, expressed in the *E. coli* transformants and purified, bind to human C1q, an enzyme linked immunosorbent assay (ELISA) was carried out as follows. As test groups, immunoglobulin constant regions produced by the HM10932 and HM10927 transformants and the derivatives prepared in the above Examples were used. As standards, a glycosylated immunoglobulin (IVIG-globulin S, Green Cross PBM) and several commercially available antibodies used as therapeutic antibodies were used. The test and standard samples were prepared in 10 mM carbonate buffer (pH 9.6) at a concentration of 1 μg/ml. The samples were aliquotted into a 96-well plate (Nunc) in an amount of 200 ng per well, and the plate was coated overnight at 4° C. Then, each well was washed with PBS-T (137 mM NaCl, 2 mM KCl, 10 mM $Na_2HPO_4$, 2 mM $KH_2PO_4$, 0.05% Tween 20) three times, blocked with 250 μl of a blocking buffer (1% bovine serum albumin in PBS-T) at room temperature for 1 hr, and washed again with the same PBS-T three times. The standard and test samples were diluted in PBS-T to a predetermined concentration and added to antibody-coated wells, and the plate was incubated at room temperature for 1 hr and washed with PBS-T three times. Thereafter, 2 μg/ml C1q (R&D Systems) was added to the plate and reacted at room temperature for 2 hrs, and the plate was washed with PBS-T six times. 200 μl of a 1:1000 dilution of a human anti-human C1q antibody-peroxidase conjugate (Biogenesis, USA) in the blocking buffer was added to each well and reacted at room temperature for 1 hr. After each well was washed with PBS-T three times, equal volumes of color reagents A and B (Color A: stabilized peroxide and Color B: stabilized chromogen; DY 999, R&D Systems) were mixed, and 200 μl of the mixture was added to each well, followed by incubation for 30 min. Then, 50 μl of a reaction termination solution, 2 M sulphuric acid, was added to each well. The plate was read using a microplate reader (Molecular Device). Absorbance of standard and test samples was measured at 450 nm, and the results are given in FIGS. 17 and 18, respectively.

When immunoglobulin subclasses were compared with each other for complement activity in their immunoglobulin Fc fragment, the highest binding affinity to C1q was found in human immunoglobulin IgG1 (Fitzgerald), the next in IgG2 (Fitzgerald) and then IgG4 (Fitzgerald), indicating that there is a difference between subclasses in complement activity. The IVIG used in this test, which is a pool of IgG subclasses, exhibited a C1q binding affinity almost the same as the purified IgG1 because IgG1 amounts to most of the IVIG. Compared to these standards, with respect to changes in binding affinity to C1q by aglycosylation, IgG1 Fc having the strongest complement activity markedly decreased when aglycosylated. IgG4 Fc, known not to induce complement activation, rarely had binding affinity to C1q, indicating that the IgG4 Fc is used as an excellent recombinant carrier with no complement activity (FIG. 17).

To determine whether the carrier maintains its property of having no binding affinity to C1q even after being conjugated to a physiologically active peptide, IFN alpha-Fc conjugates were prepared using glycosylated Fc, enzymatically deglycosylated Fc and aglycosylated recombinant Fc as carriers for IFN alpha and were evaluated for their binding affinity to C1q. A glycosylated Fc-coupled IFN alpha conjugate (IFNα-PEG-Fc: Glycosylated IgG1Fc) maintained a high binding affinity to C1q. In contrast, when interferon alpha was coupled to an Fc deglycosylated using PNGase F and other enzymes, the resulting conjugate (IFNα-PEG-DGFc: Deglycosylated IgG1Fc) displayed a markedly decreased binding affinity to C1q, which was similar to that of the *E. coli*-derived aglycosylated Fc conjugate. In addition, when the IgG1 moiety of the aglycosylated IgG1 Fc-coupled interferon alpha conjugate (IFNα-PEG-AGFcG1: Aglycosylated IgG1Fc) was exchanged with the IgG4 moiety, the resulting interferon conjugate (IFNα-PEG-FcG4 derivative 1: Aglycosylated IgG4Fc) was found to completely lose its binding affinity to C1q. When the IgG1 Fc moiety was exchanged with the IgG4 Fc monomer, the resulting conjugate (IFNα-PEG-FcG4 derivative 2: Aglycosylated IgG4Fc). These results indicate that such forms of the IgG4 Fc fragment are useful as excellent carriers not having the effector functions of antibody fragments (FIG. 18).

INDUSTRIAL APPLICABILITY

As described hereinbefore, the IgG Fc fragments of the present invention increase serum half-lives of drugs and sustain in vivo activity of drugs when used as carriers. In particular, the present IgG Fc fragments increase serum half-lives of polypeptide drugs to levels higher than any conventional modified proteins, and overcome the most significant disadvantage of conventional long-acting formulations, decreased titers, thus having blood circulation time and in vivo activity superior to albumin, previously known to be most effective. In addition, the present IgG Fc fragments have no risk of inducing immune responses. Due to these advantages, the present IgG Fc fragments are useful for developing long-acting formulations of protein drugs. Further, the long-acting formulations of protein drugs according to the present invention are capable of reducing the patient's pain from frequent injections, and maintaining serum concentrations of active polypeptides for a prolonged period of time, thus stably providing pharmaceutical efficacy.

The invention claimed is:

1. A complex of an IgG Fc fragment as a drug carrier, a non-peptide linker and a drug, wherein the IgG Fc fragment is covalently linked to the drug through the non-peptide linker, wherein the non-peptide linker is polypropylene glycol, copolymers of ethylene glycol and propylene glycol, polyoxyethylated polyols, polyvinyl alcohol, dextran, polyvinyl ether, polylactic acid, polylactic-glycolic acid, a lipid polymer, a chitin, or hyaluronic acid, and wherein the IgG Fc fragment is aglycosylated and its amino acid sequence consists of SEQ ID NO:8.

2. The complex as set forth in claim 1, wherein the aglycosylated IgG Fc fragment is a recombinant human IgG Fc fragment.

3. A composition comprising the complex of claim 1.

4. A complex of an IgG Fc fragment as a drug carrier, a non-peptide linker and a drug, wherein the IgG Fc fragment is covalently linked to the drug through the non-peptide linker, wherein the non-peptide linker is a polyethylene glycol having a molecular weight of 3.4 kDa or 10 kDa, and wherein the IgG Fc fragment is aglycosylated and its amino acid sequence consists of SEQ ID NO:8.

* * * * *

SEQUENCE LISTING

```
<160> NUMBER OF SEQ ID NOS: 26

<210> SEQ ID NO 1
<211> LENGTH: 35
<212> TYPE: DNA
<213> ORGANISM: Artificial Sequence
<220> FEATURE:
<223> OTHER INFORMATION: primer

<400> SEQUENCE: 1
cgtcatgccc agcacctgag ttcctggggg gacca                              35

<210> SEQ ID NO 2
<211> LENGTH: 42
<212> TYPE: DNA
<213> ORGANISM: Artificial Sequence
<220> FEATURE:
<223> OTHER INFORMATION: primer

<400> SEQUENCE: 2
gggggatcct catttaccca gagacaggga gaggctcttc tg                      42

<210> SEQ ID NO 3
<211> LENGTH: 12
<212> TYPE: PRT
<213> ORGANISM: Homo sapiens

<400> SEQUENCE: 3

Glu Ser Lys Tyr Gly Pro Pro Cys Pro Ser Cys Pro
  1               5                  10

<210> SEQ ID NO 4
<211> LENGTH: 663
<212> TYPE: DNA
<213> ORGANISM: homo sapiens

<400> SEQUENCE: 4
tcatgcccag cacctgagtt cctgggggga ccatcagtct tcctgttccc cccaaaaccc    60
aaggacactc tcatgatctc ccggacccct gaggtcacgt gcgtggtggt ggacgtgagc   120
caggaagacc ccgaggtcca gttcaactgg tacgtggatg gcgtggaggt gcataatgcc   180
aagacaaagc cgcgggagga gcagttcaac agcacgtacc gtgtggtcag cgtcctcacc   240
gtcctgcacc aggactggct gaacggcaag gagtacaagt gcaaggtctc caacaaaggc   300
ctcccgtcct ccatcgagaa aaccatctcc aaagccaaag gcagccccg agagccacag    360 gtgtacaccc tgcccccatc ccaggaggag atgaccaaga accaggtcag cctgacctgc   420
ctggtcaaag gcttctaccc cagcgacatc gccgtggagt gggagagcaa tgggcagccg   480
gagaacaact acaagaccac gcctcccgtg ctggactccg acggctcctt cttcctctac   540
agcaggctaa ccgtggacaa gagcaggtgg caggagggga atgtcttctc atgctccgtg   600
atgcatgagg ctctgcacaa ccactacaca cagaagagcc tctccctgtc tctgggtaaa   660
tga                                                                 663
```

<210> SEQ ID NO 5
<211> LENGTH: 69
<212> TYPE: DNA
<213> ORGANISM: homo sapiens

<400> SEQUENCE: 5
atgaaaaaga caatcgcatt tctttcttgca tctatgttcg ttttttctat tgctacaaat    60
gcccaggcg                                                              69

<210> SEQ ID NO 6
<211> LENGTH: 45
<212> TYPE: DNA
<213> ORGANISM: Artificial Sequence
<220> FEATURE:
<223> OTHER INFORMATION: primer

<400> SEQUENCE: 6
tctattgcta caaatgccca ggccttccca accattccct tatcc                      45

<210> SEQ ID NO 7
<211> LENGTH: 45
<212> TYPE: DNA
<213> ORGANISM: Artificial Sequence
<220> FEATURE:
<223> OTHER INFORMATION: primer

<400> SEQUENCE: 7
agataacgat gtttacgggt ccggaagggt tggtaaggga atagg                      45

<210> SEQ ID NO 8
<211> LENGTH: 220
<212> TYPE: PRT
<213> ORGANISM: homo sapiens

<400> SEQUENCE: 8

Ser Cys Pro Ala Pro Glu Phe Leu Gly Gly Pro Ser Val Phe Leu Phe
 1               5                  10                  15

Pro Pro Lys Pro Lys Asp Thr Leu Met Ile Ser Arg Thr Pro Glu Val
             20                  25                  30

Thr Cys Val Val Val Asp Val Ser Gln Glu Asp Pro Glu Val Gln Phe
         35                  40                  45

Asn Trp Tyr Val Asp Gly Val Glu Val His Asn Ala Lys Thr Lys Pro
     50                  55                  60

Arg Glu Glu Gln Phe Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Gly Leu Pro Ser Ser Ile Glu Lys Thr Ile Ser Lys Ala
            100                 105                 110

Lys Gly Gln Pro Arg Glu Pro Gln Val Tyr Thr Leu Pro Pro Ser Gln
        115                 120                 125

Glu Glu Met Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Arg Leu Thr Val Asp Lys Ser Arg Trp Gln Glu
            180                 185                 190

Gly Asn Val Phe Ser Cys Ser Val Met His Glu Ala Leu His Asn His
            195                 200                 205

Tyr Thr Gln Lys Ser Leu Ser Leu Ser Leu Gly Lys
    210                 215                 220

<210> SEQ ID NO 9
<211> LENGTH: 654
<212> TYPE: DNA
<213> ORGANISM: homo sapiens

<400> SEQUENCE: 9
gcacctgagt tcctgggggg accatcagtc ttcctgttcc ccccaaaacc caaggacact     60
ctcatgatct cccggacccc tgaggtcacg tgcgtggtgg tggacgtgag ccaggaagac    120
cccgaggtcc agttcaactg gtacgtggat ggcgtggagg tgcataatgc caagacaaag    180
ccgcgggagg agcagttcaa cagcacgtac cgtgtggtca gcgtcctcac cgtcctgcac    240
caggactggc tgaacggcaa ggagtacaag tgcaaggtct ccaacaaagg cctcccgtcc    300
tccatcgaga aaccatctcc aaagccaaa gggcagcccc gagagccaca ggtgtacacc    360
ctgcccccat cccaggagga gatgaccaag aaccaggtca gcctgacctg cctggtcaaa    420
ggcttctacc ccagcgacat cgccgtggag tgggagagca tgggcagcc ggagaacaac    480 tacaagacca cgcctcccgt gctggactcc gacggctcct tcttcctcta cagcaggcta    540
accgtggaca gagcaggtg gcaggagggg aatgtcttct catgctccgt gatgcatgag    600
gctctgcaca accactacac acagaagagc ctctccctgt ctctgggtaa atga          654

<210> SEQ ID NO 10
<211> LENGTH: 217
<212> TYPE: PRT
<213> ORGANISM: homo sapiens

<400> SEQUENCE: 10

Ala Pro Glu Phe Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
                 20                  25                  30

Val Val Asp Val Ser Gln Glu Asp Pro Glu Val Gln Phe Asn Trp Tyr
             35                  40                  45

Val Asp Gly Val Glu Val His Asn Ala Lys Thr Lys Pro Arg Glu Glu
         50                  55                  60

Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly Lys
    210                 215

<210> SEQ ID NO 11
<211> LENGTH: 33
<212> TYPE: DNA
<213> ORGANISM: Artificial Sequence
<220> FEATURE:
<223> OTHER INFORMATION: primer

<400> SEQUENCE: 11
cgccgtgccc agcacctgaa ctcctggggg gac                                33

<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
gggggatcct catttacccg gagacaggga gag                                33

<210> SEQ ID NO 13
<211> LENGTH: 15
<212> TYPE: PRT
<213> ORGANISM: homo sapiens

<400> SEQUENCE: 13

Glu Pro Lys Ser Cys Asp Lys Thr His Thr Cys Pro Pro Cys Pro
 1               5                  10                  15

<210> SEQ ID NO 14
<211> LENGTH: 660
<212> TYPE: DNA
<213> ORGANISM: homo sapiens

<400> SEQUENCE: 14
ccgtgcccag cacctgaact cctggggggga ccgtcagtct tcctcttccc cccaaaaccc      60
aaggacaccc tcatgatctc ccggaccccct gaggtcacat gcgtggtggt ggacgtgagc    120
cacgaagacc ctgaggtcaa gttcaactgg tacgtggacg gcgtggaggt gcataatgcc    180
aagacaaagc cgcgggagga gcagtacaac agcacgtacc gtgtggtcag cgtcctcacc    240
gtcctgcacc aggactggct gaatggcaag gagtacaagt gcaaggtctc caacaaagcc    300
ctcccagccc ccatcgagaa aaccatctcc aaagccaaag gcagccccg agagccacag     360 gtgtacaccc tgcccccatc ccgggatgag ctgaccaaga accaggtcag cctgacctgc    420
ctggtcaaag gcttctatcc cagcgacatc gccgtggagt gggagagcaa tgggcagccg    480
gagaacaact acaagaccac gcctcccgtg ctggactccg acggctcctt cttcctctac    540
agcaagctca ccgtggacaa gagcaggtgg cagcagggga acgtcttctc atgctccgtg    600
atgcatgagg ctctgcacaa ccactacacg cagaagagcc tctccctgtc tccgggtaaa    660

<210> SEQ ID NO 15
<211> LENGTH: 220
<212> TYPE: PRT
<213> ORGANISM: homo sapiens -continued

<400> SEQUENCE: 15

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65              70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 16
<211> LENGTH: 26
<212> TYPE: DNA
<213> ORGANISM: Artificial Sequence
<220> FEATURE:
<223> OTHER INFORMATION: primer

<400> SEQUENCE: 16
cggcacctga actcctgggg ggaccg                                            26

<210> SEQ ID NO 17
<211> LENGTH: 651
<212> TYPE: DNA
<213> ORGANISM: homo sapiens

<400> SEQUENCE: 17
gcacctgaac tcctgggggg accgtcagtc ttcctcttcc ccccaaaacc caaggacacc        60
ctcatgatct cccggacccc tgaggtcaca tgcgtggtgg tggacgtgag ccacgaagac       120
cctgaggtca agttcaactg gtacgtggac ggcgtggagg tgcataatgc aagacaaag        180 ccgcgggagg agcagtacaa cagcacgtac cgtgtggtca gcgtcctcac cgtcctgcac       240
caggactggc tgaatggcaa ggagtacaag tgcaaggtct ccaacaaagc cctcccagcc       300
cccatcgaga aaaccatctc caaagccaaa gggcagcccc gagagccaca ggtgtacacc       360 ctgccccat cccgggatga gctgaccaag aaccaggtca gcctgacctg cctggtcaaa       420
ggcttctatc ccagcgacat cgccgtggag tgggagagca atgggcagcc ggagaacaac       480

-continued

```
tacaagacca cgcctcccgt gctggactcc gacggctcct tcttcctcta cagcaagctc      540
accgtggaca agagcaggtg gcagcagggg aacgtcttct catgctccgt gatgcatgag      600
gctctgcaca accactacac gcagaagagc ctctccctgt ctccgggtaa a              651
```

<210> SEQ ID NO 18
<211> LENGTH: 217
<212> TYPE: PRT
<213> ORGANISM: homo sapiens

<400> SEQUENCE: 18

```
Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 19
<211> LENGTH: 29
<212> TYPE: DNA
<213> ORGANISM: Artificial Sequence
<220> FEATURE:
<223> OTHER INFORMATION: primer

<400> SEQUENCE: 19

```
cgccgtgccc agcacctccg gtggcggga                                        29
```

<210> SEQ ID NO 20
<211> LENGTH: 33
<212> TYPE: DNA
<213> ORGANISM: Artificial Sequence
<220> FEATURE:
<223> OTHER INFORMATION: primer

<400> SEQUENCE: 20

```
gggggatcct catttacccg gagacaggga gag                                   33
```

```
<210> SEQ ID NO 21
<211> LENGTH: 12
<212> TYPE: PRT
<213> ORGANISM: homo sapiens

<400> SEQUENCE: 21

Glu Arg Lys Cys Cys Val Glu Cys Pro Pro Cys Pro
 1               5                  10

<210> SEQ ID NO 22
<211> LENGTH: 657
<212> TYPE: PRT
<213> ORGANISM: homo sapiens

<400> SEQUENCE: 22

Cys Cys Gly Thr Gly Cys Cys Ala Gly Cys Ala Cys Cys Thr Cys
 1               5                  10                  15

Cys Gly Gly Thr Gly Gly Cys Gly Gly Ala Cys Cys Gly Thr Cys
                20                  25                  30

Ala Gly Thr Cys Thr Thr Cys Cys Thr Cys Thr Cys Cys Cys
                35                  40                  45

Cys Cys Ala Ala Ala Ala Cys Cys Ala Ala Gly Gly Ala Cys Ala
                50                  55                  60

Cys Cys Thr Cys Ala Thr Gly Ala Thr Cys Thr Cys Cys Gly
 65                  70                  75                  80

Gly Ala Cys Cys Cys Thr Gly Ala Gly Thr Cys Ala Cys Ala
                85                  90                  95

Thr Gly Cys Gly Thr Gly Gly Thr Gly Gly Thr Gly Ala Cys Gly
                100                 105                 110

Thr Gly Ala Gly Cys Cys Ala Cys Gly Ala Ala Gly Ala Cys Cys Cys
                115                 120                 125

Thr Gly Ala Gly Gly Thr Cys Cys Ala Gly Thr Thr Cys Ala Ala Cys
                130                 135                 140

Thr Gly Gly Thr Ala Cys Gly Thr Gly Gly Ala Cys Gly Gly Cys Gly
145                 150                 155                 160

Thr Gly Gly Ala Gly Gly Thr Gly Cys Ala Thr Ala Ala Thr Gly Cys
                165                 170                 175

Cys Ala Ala Gly Ala Cys Ala Ala Gly Cys Cys Gly Cys Gly Gly
                180                 185                 190

Gly Ala Gly Gly Ala Gly Cys Ala Gly Thr Thr Ala Ala Cys Ala
                195                 200                 205

Gly Cys Ala Cys Gly Thr Thr Thr Cys Gly Thr Gly Thr Gly Gly Thr
                210                 215                 220

Cys Ala Gly Cys Gly Thr Cys Cys Thr Cys Ala Cys Cys Gly Thr Cys
225                 230                 235                 240

Gly Thr Gly Cys Ala Cys Cys Ala Gly Ala Cys Thr Gly Gly Cys
                245                 250                 255

Thr Gly Ala Ala Thr Gly Gly Cys Ala Ala Gly Gly Ala Gly Thr Ala
                260                 265                 270

Cys Ala Ala Gly Thr Gly Cys Ala Ala Gly Gly Thr Cys Thr Cys Cys
                275                 280                 285

Ala Ala Cys Ala Ala Ala Gly Gly Cys Cys Thr Cys Cys Cys Ala Gly
                290                 295                 300

Cys Cys Cys Cys Cys Ala Thr Cys Gly Ala Gly Ala Ala Ala Cys
305                 310                 315                 320
```

Cys Ala Thr Cys Thr Cys Cys Ala Ala Ala Cys Cys Ala Ala Ala
                325                 330                 335

Gly Gly Gly Cys Ala Gly Cys Cys Cys Gly Ala Gly Ala Gly Cys
            340                 345                 350

Cys Ala Cys Ala Gly Gly Thr Gly Thr Ala Cys Ala Cys Cys Thr
            355                 360                 365

Gly Cys Cys Cys Cys Ala Thr Cys Cys Gly Gly Gly Ala Ala
        370                 375                 380

Gly Ala Gly Ala Thr Gly Ala Cys Cys Ala Ala Gly Ala Ala Cys Cys
385                 390                 395                 400

Ala Gly Gly Thr Cys Ala Gly Cys Cys Thr Gly Ala Cys Cys Thr Gly
                405                 410                 415

Cys Cys Thr Gly Gly Thr Cys Ala Ala Ala Gly Gly Cys Thr Thr Cys
                420                 425                 430

Thr Ala Thr Cys Cys Ala Gly Cys Gly Ala Cys Ala Thr Cys Gly
        435                 440                 445

Cys Cys Gly Thr Gly Gly Ala Gly Thr Gly Gly Ala Gly Ala Gly
        450                 455                 460

Cys Ala Ala Thr Gly Gly Gly Cys Ala Gly Cys Cys Gly Gly Ala Gly
465                 470                 475                 480

Ala Ala Cys Ala Ala Cys Thr Ala Cys Ala Ala Gly Ala Cys Cys Ala
                485                 490                 495

Cys Gly Cys Cys Thr Cys Cys Ala Thr Gly Cys Thr Gly Gly Ala
        500                 505                 510

Cys Thr Cys Cys Gly Ala Cys Gly Gly Cys Thr Cys Cys Thr Thr Cys
        515                 520                 525

Thr Thr Cys Cys Thr Cys Thr Ala Cys Ala Gly Cys Ala Ala Gly Cys
530                 535                 540

Thr Cys Ala Cys Cys Gly Thr Gly Gly Ala Cys Ala Ala Gly Ala Gly
545                 550                 555                 560

Cys Ala Gly Gly Thr Gly Gly Cys Ala Gly Cys Ala Gly Gly Gly
                565                 570                 575

Ala Ala Cys Gly Thr Cys Thr Thr Cys Thr Cys Ala Thr Gly Cys Thr
            580                 585                 590

Cys Cys Gly Thr Gly Ala Thr Gly Cys Ala Thr Gly Ala Gly Gly Cys
        595                 600                 605

Thr Cys Thr Gly Cys Ala Cys Ala Ala Cys Cys Ala Cys Thr Ala Cys
        610                 615                 620

Ala Cys Gly Cys Ala Gly Ala Ala Gly Ala Gly Cys Cys Thr Cys Thr
625                 630                 635                 640

Cys Cys Cys Thr Gly Thr Cys Thr Cys Cys Gly Gly Gly Thr Ala Ala
                645                 650                 655

Ala

<210> SEQ ID NO 23
<211> LENGTH: 219
<212> TYPE: PRT
<213> ORGANISM: homo sapiens

<400> SEQUENCE: 23

Pro Cys Pro Ala Pro Val Ala Gly Pro Ser Val Phe Leu Phe Pro
 1               5                  10                  15

Pro Lys Pro Lys Asp Thr Leu Met Ile Ser Arg Thr Pro Glu Val Thr
            20                  25                  30

```
Cys Val Val Asp Val Ser His Glu Asp Pro Glu Val Gln Phe Asn
         35                  40                  45

Trp Tyr Val Asp Gly Val Glu Val His Asn Ala Lys Thr Lys Pro Arg
     50                  55                  60

Glu Glu Gln Phe Asn Ser Thr Phe Arg Val Val Ser Val Leu Thr Val
 65                  70                  75                  80

Val His Gln Asp Trp Leu Asn Gly Lys Glu Tyr Lys Cys Lys Val Ser
                 85                  90                  95

Asn Lys Gly Leu Pro Ala Pro Ile Glu Lys Thr Ile Ser Lys Thr Lys
            100                 105                 110

Gly Gln Pro Arg Glu Pro Gln Val Tyr Thr Leu Pro Pro Ser Arg Glu
        115                 120                 125

Glu Met Thr Lys Asn Gln Val Ser Leu Thr Cys Leu Val Lys Gly Phe
    130                 135                 140

Tyr Pro Ser Asp Ile Ala Val Glu Trp Glu Ser Asn Gly Gln Pro Glu
145                 150                 155                 160

Asn Asn Tyr Lys Thr Thr Pro Pro Met Leu Asp Ser Asp Gly Ser Phe
                165                 170                 175

Phe Leu Tyr Ser Lys Leu Thr Val Asp Lys Ser Arg Trp Gln Gln Gly
            180                 185                 190

Asn Val Phe Ser Cys Ser Val Met His Glu Ala Leu His Asn His Tyr
        195                 200                 205

Thr Gln Lys Ser Leu Ser Leu Ser Pro Gly Lys
    210                 215

<210> SEQ ID NO 24
<211> LENGTH: 10
<212> TYPE: PRT
<213> ORGANISM: Homo sapiens

<400> SEQUENCE: 24

Pro Cys Pro Ala Pro Glu Leu Leu Gly Gly
 1               5                  10

<210> SEQ ID NO 25
<211> LENGTH: 10
<212> TYPE: PRT
<213> ORGANISM: Homo sapiens

<400> SEQUENCE: 25

Ser Cys Pro Ala Pro Glu Phe Leu Gly Gly
 1               5                  10

<210> SEQ ID NO 26
<211> LENGTH: 10
<212> TYPE: PRT
<213> ORGANISM: Homo sapiens

<400> SEQUENCE: 26

Pro Cys Pro Ala Pro Pro Val Ala Gly Pro
 1               5                  10
```